US008524246B2

(12) United States Patent
Rottiers et al.

(10) Patent No.: US 8,524,246 B2
(45) Date of Patent: Sep. 3, 2013

(54) **TREATMENT OF IMMUNE DISEASE BY MUCOSAL DELIVERY OF ANTIGENTS USING GENETICALLY MODIFIED *LACTOBACILLUS***

(71) Applicant: Actogenix NV, Zwijnaarde (BE)

(72) Inventors: Pieter Rottiers, De Pinte (BE); Veerle Snoeck, Zingem (BE)

(73) Assignee: Actogenix N.V., Zwijnaarde (BE)

( * ) Notice: Subject to any disclaimer, the term of this patent is extended or adjusted under 35 U.S.C. 154(b) by 0 days.

(21) Appl. No.: 13/720,967

(22) Filed: Dec. 19, 2012

(65) Prior Publication Data
US 2013/0095129 A1    Apr. 18, 2013

Related U.S. Application Data

(62) Division of application No. 12/448,921, filed on Jul. 14, 2009, now abandoned.

(30) Foreign Application Priority Data

Jan. 25, 2007  (EP) ..................... 07447006
Jul. 19, 2007  (EP) ..................... 07112792
Jan. 25, 2008  (EP) ............... PCT/EP2008/050900

(51) Int. Cl.
*A61K 39/02* (2006.01)
*A61K 39/00* (2006.01)
*A61K 38/00* (2006.01)
*A01N 63/00* (2006.01)

(52) U.S. Cl.
USPC .......... 424/200.1; 424/93.45; 424/190.1; 424/184.1; 424/93.2; 514/1.1

(58) Field of Classification Search
None
See application file for complete search history.

(56) References Cited

U.S. PATENT DOCUMENTS

| | | |
|---|---|---|
| 4,100,495 A | 7/1978 | Luvison et al. |
| 4,190,495 A | 2/1980 | Curtiss, III |
| 4,888,170 A | 12/1989 | Curtiss, III |
| 5,032,510 A | 7/1991 | Kovacevic et al. |
| 5,149,532 A | 9/1992 | Brunell |
| 5,240,705 A | 8/1993 | Jacobs |
| 5,288,703 A | 2/1994 | Wilmore |
| 5,330,753 A | 7/1994 | Mekalanos et al. |
| 5,364,774 A | 11/1994 | Muir et al. |
| 5,401,642 A | 3/1995 | Fiers et al. |
| 5,401,658 A | 3/1995 | Fiers et al. |
| 5,417,986 A | 5/1995 | Reid et al. |
| 5,455,034 A | 10/1995 | Nagaraja et al. |
| 5,504,005 A | 4/1996 | Bloom et al. |
| 5,547,664 A | 8/1996 | Charles et al. |

(Continued)

FOREIGN PATENT DOCUMENTS

CN  200510069598.0   11/2005
DE  42 31 764 A1     3/1994

(Continued)

OTHER PUBLICATIONS

U.S. Appl. No. 60/353,923, filed Jan. 31, 2002, Chen.

(Continued)

*Primary Examiner* — S. Devi
(74) *Attorney, Agent, or Firm* — TraskBritt

(57) ABSTRACT

The present invention relates to the treatment of autoimmune and allergic diseases by mucosal delivery by micro-organism, in particular *Lactococcus lactis*, of secreted immunodominant antigens.

15 Claims, 7 Drawing Sheets

(56) References Cited

U.S. PATENT DOCUMENTS

| | | | |
|---|---|---|---|
| 5,559,007 | A | 9/1996 | Suri et al. |
| 5,591,632 | A | 1/1997 | O'Donnell et al. |
| 5,733,540 | A | 3/1998 | Lee |
| 5,753,622 | A | 5/1998 | Buret et al. |
| 5,824,538 | A | 10/1998 | Branstrom et al. |
| 5,837,509 | A | 11/1998 | Israelsen et al. |
| 5,972,685 | A | 10/1999 | Beitz et al. |
| 5,972,887 | A | 10/1999 | Schwartz |
| 6,100,388 | A | 8/2000 | Casas et al. |
| 6,130,082 | A | 10/2000 | Majarian et al. |
| 6,190,662 | B1 | 2/2001 | Steidler et al. |
| 6,190,669 | B1 | 2/2001 | Noriega et al. |
| 6,221,648 | B1 | 4/2001 | Le Page et al. |
| 6,261,561 | B1 | 7/2001 | Stewart et al. |
| 6,262,119 | B1 | 7/2001 | Ferrante et al. |
| 6,605,286 | B2 | 8/2003 | Steidler |
| 6,610,300 | B1 | 8/2003 | Segers et al. |
| 6,656,907 | B1 | 12/2003 | Buret et al. |
| 6,685,943 | B1 | 2/2004 | Hook et al. |
| 6,746,671 | B2 | 6/2004 | Steidler et al. |
| 7,358,067 | B2 | 4/2008 | Vrang et al. |
| 7,601,799 | B2 | 10/2009 | Steidler |
| 2001/0006642 | A1 | 7/2001 | Steidler et al. |
| 2002/0019043 | A1 | 2/2002 | Steidler et al. |
| 2003/0202991 | A1 | 10/2003 | Steidler et al. |
| 2003/0203472 | A1 | 10/2003 | Portnoy et al. |
| 2004/0043003 | A1 | 3/2004 | Chen et al. |
| 2004/0247581 | A1 | 12/2004 | Bronstad et al. |
| 2005/0101005 | A1 | 5/2005 | Steidler |
| 2005/0276788 | A1 | 12/2005 | Steidler et al. |

FOREIGN PATENT DOCUMENTS

| | | |
|---|---|---|
| EP | 0 176 320 | 4/1986 |
| EP | 0 406 003 A1 | 1/1991 |
| EP | 0 449 770 | 10/1991 |
| EP | 0 450 176 | 10/1991 |
| EP | 1 092 437 A1 | 4/2001 |
| EP | 1 319 410 A1 | 6/2003 |
| WO | WO 88/06626 | 9/1988 |
| WO | WO 91/06654 | 5/1991 |
| WO | WO 93/17117 | 9/1993 |
| WO | WO 95/03418 | 2/1995 |
| WO | WO 95/10614 | 4/1995 |
| WO | WO 95/10621 | 4/1995 |
| WO | WO 96/11277 | 4/1996 |
| WO | WO 96/32487 A1 | 10/1996 |
| WO | WO 96/40947 | 12/1996 |
| WO | WO 97/14806 | 4/1997 |
| WO | WO 98/31786 | 7/1998 |
| WO | WO 99/58652 | 11/1999 |
| WO | WO 00/18377 | 4/2000 |
| WO | WO 00/22909 | 4/2000 |
| WO | WO 00/23471 | 4/2000 |
| WO | WO 02/090551 A2 | 11/2002 |
| WO | WO 03/096979 A | 11/2003 |
| WO | WO 04/001020 A2 | 12/2003 |
| WO | WO 2004/045392 A | 6/2004 |
| WO | WO 2004/046346 | 6/2004 |
| WO | WO 2007/063075 A | 6/2007 |
| WO | WO 2008/090223 A2 | 7/2008 |

OTHER PUBLICATIONS

U.S. Appl. No. 60/353,964, filed Jan. 31, 2002, Chen.
U.S. Appl. No. 60/353,885, filed Jan. 31, 2002, Chen.
U.S. Appl. No. 60/401,465, filed Aug. 5, 2002, Chen.
Anderson, Human gene therapy, 1998, Nature, vol. 392.
Arslanoglu et al., 1998, Biotechnology Letters, pp. 917-921, vol. 20.
ATCC Catalog Search performed online on Nov. 17, 2009 at www.atcc.org/ATCCAdvanceCatalogSearch/tabid/112/default.aspx.
Bamba et al., Gastroenterol J., 1993, pp. 511-517, vol. 28, No. 4.
Barbara et al., interleukin 10 gene transfer prevents experimental colitis rats, 2000, Gut, pp. 344-349, vol. 46.
Bellini et al., Producation process of recombinant IL-1 beta from *Bacillus subtilis*: comparison between intracellular and exocellular expression, 1991, Journal of Biotechnology, pp. 177-192, vol. 18.
Bermudez-Humaran et al., J. Medical Microbiology, 2004, 53:427-433.
Bijlsma et al., Trends in Microbiology, 2003, 11/8:359-366.
Billman-Jacobe., Current Opinion in Biotechnology, 1996, 7:500-504.
Blast, Basic Local Alignment Search Tool, visited Jul. 7, 2009, <http://blast.ncbi.nlm.nih.gov/Blast.cgi.
Bojovic et al., Applied & Environ. Microbiol 57/2:385-388 (1991).
Brett et al., Eur. J. Immunol., 23:1608-1614 (1993).
Chen et al., FEMS Microbiology Letters, 2003, 229:111-117.
Claverys et al., Gene, 1995, 164:123-128.
Curtiss Tables III, IV and V, from U.S. Patent 4,888,170.
Cytokines Final Brochure for Cytokine Therapies, The Food and Drug Administration and the New York Academy of Sciences, held on Mar. 26-27, 2009.
Darji et al., J. Biotechnology, 1995, 43:205-212.
Designing bacteria and white cells to deliver drugs to the gut, The Lancet, Sep. 20, 2003, www.thelancet.com, vol. 362, p. 964-965.
Edwards et al., Infection & Immunity, 60/6:2514-2521 (1992).
Eizaguirre et al., Abstract, Effect of Growth Hormone, Epidermal Growth Factor, and Insulin and Bacterial Translocation in Experimental Short Bowel Syndrome, Journal of Pediatric Surgery, 2000, pp. 692-695, vol. 35, No. 5.
Elliott et al., Bacterial colonization and healing of gastric ulcers: the effects of epiderinal growth factor, Am. J. Physiol. Gastrointest. Liver Physiol., 2000, pp. G105-G112, vol. 278.
English translation of the Japanese Office Action dated Apr. 7, 2009.
Farrell et al., FEMS Microbiology Letters, 1995, 130:81-85.
Figler et al., Archives Biochemistry and Biophysics, 2000, 376/1:34-46.
Fischetti et al., Current Opinion in Biotechnology, Oct. 1993, 4/5:603-610.
Fu et al., "Development of a chromosome-plasmid balanced lethal system for *Lactobacillus acidophilus* with thyA gene as selective marker," Microbiol. Immunol., 2000, pp. 551-556, vol. 44, No. 7.
Gasson, Abstract, "In vivo genetic systems in lactic acid bacteria," FEMS Microbiol., 1990, Rev. 87:43-60.
Gotz, J. Applied Bacteriology Symposium Supplement, 1990, 49S-53S.
Gutierrez et al., Appl. Microbiol. Biotechnol., 2006, 72/1:41-51.
Hansson et al., J. Bacteriology, Jul. 1992, 174/13:4239-4245.
Hardin et al., Gut, 1999, pp. 26-32, vol. 44.
Hazebrouck et al., Applied and Environmental Microbiology, Dec. 2006, 72/12:7460-7467.
Heath et al., Abstract, Cytokines as immunological adjuvants, Vaccine, 1992, pp. 427-434, vol. 10, No. 7.
Hegedus et al., Gene, 1998, 207:241-249.
Herfarth et al., Interleukin 10 suppresses experimental chronic, granulomatous inflammation induced by bacterial cell wall polymers, 1996, GUT, pp. 836-845, vol. 39.
Holmes et al., Infection & Immunity, 66/10:4633-4639 (1998).
Huibregtse et al., Abstract, Induction of Antigen-specific Oral Tolerance by Genetically Modified *Lactococcus lactis* Delivering DQ8-specific Immunodominant Gliadin Epitopes to Gluten-sensitized Class II Transgenic Mice, Clinical Immunology, Jan. 1, 2007, pp. S53-S54, vol. 123.
Huibregtse et al. Clinical Immunology 123; S53-S54, F.116, Jan. 1, 2007, Available online May 10, 2007.
Huibregtse et al. Gastroenterology 130: 4 Suppl. #T1765, A557, 2006.
Huibregtse et al., Induction of Antigen-specific Oral Tolerance by Genetically Modified *Lactococcus lactis* Delivering DQ80specific Immunodominant Gliadin Epitopes to Gluten-sensitized Class II Transgenic Mice, Clinical Immunology, May 10, 2007, pp. S53-S54, vol. 123.
Huibregtse et al., Mucosa delivery of ovalbumin by the genetically modified *L. lactis* suppresses systemic and local inflammatory T-cell responses in DO11.10 mice, Gastroenterology, Apr. 2006, pp. A557, vol. 130, No. 4, Suppl. 2.
Iwaki et al., Infection Immunity, 58/9:2929-2934 (1990).

Janssen et al., Microbial Pathogenesis, 1995, 19:193-201.
Jeong et al., Food Microbiology, 2006, 23:82-89.
Kagnoff, Martin F., Overview and Pathogenesis of Celiac Disease, Gastroenterology, 2005, pp. 810-818, vol. 128.
Karolien et al. Gastroenterology 132: Suppl. 2: A564, Apr. 2002.
Karolien et al. FASEB Journal 20: A1095, Mar. 2006.
Kingman, Trial Tests If Modified Bacteria Can Deliver to Gut Mucosa, Nature Biotechnology, Jun. 15, 2003, online.
Kitchener, Prisons without bars, Nature Reviews, Genetics, Aug. 2003, p. 577, vol. 4.
Koivula et al., Isolation and Characterization of *Lactococcus lactis* subsp. lactis Promoters, Applied and Environmental Microbiology, Feb. 1991, pp. 333-340, vol. 57, No. 2.
Kong et al., Secretion of Human Interleukin 2 by Recombinant *Mycobacterium bovis* BCG, Infection and Immunity, Mar. 1995, pp. 799-803, vol. 63, No. 3.
Korelitz et al., Immunosuppressive therapy of inflammatory bowel disease: A historical perspective.
Kruisselbrink et al., Recombinant *Lactobacillus* Plantarum Inhibits Ouse Dust Mite-Specific T-Cell Responses, Clinical and Experimental Immunology, Oct. 1, 2001, pp. 2-8, vol. 126, No. 1.
Kuby, Cytokine receptors, 1994, Immunology, pp. 304-306.
Kurahayashi et al., Effects of EGF administration in the intestinal adaptation in the rat after massive intestinal resection, Diagnostics and New Medicaments, 1991, pp. 1691-1701, vol. 28, No. 9.
Leach et al., The role of IL-10 in inflammatory bowel disease: "Of mice and men," 1999, Toxicologic Pathology, pp. 123-133.
Leenhouts et al., Applied and Environmental Microbiology, Dec. 1998, 64/12:4736-4742.
Leenhouts et al., Applied and Environmental Microbiology, Sep. 1991, 57/9:2568-2575.
Leenhouts et al., I. Bacteriology, Aug. 1991, 173-15:4794-4798.
Leong et al., Selective Induction of Immune Responses by Cytokines Coexpressed in Recombinant Fowlpox Virus, Journal of Virology, Dec. 1994, pp. 8125-8130, vol. 68, No. 12.
Leong-Morgenthaler et al., Lactose Metabolism in *Lactobacillus bulgaricus*: Analysis of the Primary Structure and Expression of the Genes Involved, Journal of Bacteriology, Mar. 1991, pp. 1951-1957, vol. 173. No. 6.
Liu et al., J. Applied Microbiology, 2005, 98:127-135.
Maassen et al., Reduced experimental autoimmune encephalomyelitis after intranasal and oral administration of recombinant *lactobacilli* expressing myelin antigens, Vaccine, Dec. 1, 2003, pp. 4685-4693, vol. 21, No. 32.
Mayer et al., Abstract, Therapeutic potential of oral tolerance, Nature Reviews Immunology, Jun. 2004, pp. 407-419. vol. 4, No. 6.
McCluskie et al., Route and method of delivery of DNA vaccine influence immune responses in mice and non-human primates, 1999, Molecular Medicine, pp. 287-300, vol. 5.
Merriam-Webster's Collegiate Dictionary, Tenth Edition, Springfield, Massachusetts, USA, 2001, p. 922.
Motamedi et al., Gene, 1995, 160:25-31.
Norton et al., FEMS Immunology and Medical Microbiology, 1996, 14:167-177.
Norton et al., FEMS Microbiology Letters, 1994, 120/3:249-256.
Norton et al., Progress in the Development of *Lactococcus lactis* as a Recombinant Mucosal Vaccine Delivery System, Folia Microbiologica, Jan. 1, 1995, pp. 225-230, vol. 40, No. 3.
Norton et al., Vaccine, 1997, 15(6/7):616-619.
Notice of Allowance for U.S. Appl. No. 10/687,996, dated Jun. 15, 2010.
Nottebrock et al., Thymidine Concentrations in Serum and Urine of Different Animal Species and Man, Biochemical Pharmacology, 1977, pp. 2175-2179, vol. 26, Pergamon Press, Great Britain.
Office Action for U.S. Appl. No. 10/687,996, dated Jun. 6, 2006.
Office Action for U.S. Appl. No. 10/687,996, dated Jan. 30, 2007.
Office Action for U.S. Appl. No. 10/687,996, dated Jul. 26, 2007.
Office Action for U.S. Appl. No. 10/687,996, dated Jul. 17, 2008.
Office Action for U.S. Appl. No. 10/687,996, dated Mar. 19, 2009.
Office Action for U.S. Appl. No. 10/687,996, dated Nov. 30, 2009.
Office Action for U.S. Appl. No. 11/127,921, dated Jul. 9, 2008.
Office Action for U.S. Appl. No. 11/127,921, dated Mar. 10, 2009.
Office Action for U.S. Appl. No. 11/127,921, dated Mar. 16, 2010.
Oggioni et al., Gene, 1996, 169:85-90.
Oggioni et al., Vaccine, 1995, 13/8:775-779.
Paccez et al., Vaccine, 2007, 24:4671-4680.
Page et al., Innovations in oral gene delivery: challenges and potentials, 2001, DDT, pp. 92-101, vol. 6.
Papadakis et al., Role of cytokine in the pathogenesis of inflammatory bowel disease, 2000, Annu. Rev. Med., vol. 51, pp. 289-298.
PCT International Preliminary Examination Report, PCT/EP02/04942, dated Sep. 16, 2003, 5 pages.
PCT International Preliminary Examination Report, PCT/EP03/50832, dated Jul. 6, 2004.
PCT International Search Report, PCT/EP02/04942, dated Jan. 13, 2003, 2 pages.
PCT International Search Report, PCT/EP03/50832, dated Jun. 4, 2004.
PCT International Search Report, PCT/EP2005/052296, dated Sep. 5, 2005.
PCT International Search Report, PCT/EP2008/050900, dated Nov. 24, 2008.
Platteeuw et al., Applied and Environmental Microbiology, 1996, 62/3:1008-1013.
Ross et al., Cloning and Characterization of the Thymidylate Synthase Gene from *Lactococcus lactis* subsp. lactis, Applied and Environmental Microbiology, Jul. 1990, pp. 2156-2163, vol. 56, No. 7.
Ross et al., Thymidylate Synthase Gene from *Lactococcus lactis* as a Genetic Marker: an Alternative to Antibiotic Resistance Genes, Applied and Environmental Microbiology, Jul. 1990, pp. 2164-2169, vol. 56, No. 7.
Salzet, Michel, "Leech Thrombin Inhibitors," Current Pharmaceutical Design, 2002, pp. 493-503, vol. 8.
Samuelson et al., J. Bacteriology, Mar. 1995, 177/6:1470-1476.
Sasaki et al., "thyA as a Selection Marker in Construction of Food-Grade Host-Vector and Integration Systems for *Streptococcus thermophilus*," Applied and Environmental Microbiology, Mar. 2004, pp. 1858-1864, vol. 70, No. 3.
Schotte et al., Secretion of biologically active murine interleukin-10 by *Lactococcus lactis*, Enzyme and Microbial Technology, 2000, pp. 761-765, vol. 27.
Scott et al., Abstract, FEMS Microbiology Ecology, Aug. 1998, 26/3:219-230.
Sham et al., Abstract, Epidermal Growth Factor Improves Nutritional Outcome in a Rat Model of Short Bowel Syndrome, Journal of Pediatric Surgery, 2002, pp. 765-769, vol. 37, No. 5.
Slos et al., FEMS Microbiology Letters, 1998, 169:29-36.
Pouwels et al., Genetics of *lactobacilli*: plasmids and gene expression, 1993, Anionic Van Leeuwenhoek, pp. 85-107, vol. 64.
Pouwels et al., International J. Food Microbiology, 1998, 41:155-167.
Pouwels et al., J. Biotechnology, 1996, 44:183-192.
Pozzi et al., Abstract, Research in Microbiology, 1990, 141/6:659-670.
Pozzi et al., Abstract, Research in Microbiology, 1992, 143/5:449-457.
Pozzi et al., Infection and Immunity, May 1992, 60/5:1902-1907.
Ramasany et al., Vaccine, 2006, 24:3900-08.
Rao et al., Eur. J. Pharmacol., 1996, pp. 209-212, vol. 303, No. 3.
Rapoport, Current Opinion in Biotechnology, 1:21-27 (1990).
Reviriego et al., International Dairy Journal, 2007, 17-574-577.
Robinson et al., Nature Biotechnology, 1997, 15:653-57.
Rodriguez et al., International J. Food Microbiology, 2003, 80:101-116.
Office Action for U.S. Appl. No. 11/127,921, dated Oct. 30, 2007.
PCT International Search Report, PCT/EP03/50242, dated Jan. 15, 2004.
Senger et al. Immunology Letters 88: 127-134, 2003.
Shi Da et al., Progress on *Lactococcus lactis* expressing heterologous antigens as live mucosal vaccines, Acta Microbiologica Sinica, 2006, vol. 46, No. 4, Aug. 4, 2006.
Sibakov et al., Applied & Environ. Microbiol., 57/2:341-348 (1991).
Steidler et al., Biological containment of genetically modified *Lactococcus lactis* for intestinal delivery of human interleukin 10, Nature Biotechnology, Jul. 2003, pp. 785-789, vol. 21, No. 7.

Steidler et al., J. Bacteriol. 175/23:7639-7643 (1993).
Steidler et al., Mucosal Delivery of Murine Interleukin-2 (IL-2) and IL-6 by recombinant Strains of *Lactococcus lactis* Coexpressing Antigen and Cytokine, Infection and Immunity, 1998, pp. 3183-3189 vol. 66, No. 7.
Steidler et al., NATO ASI Series vol. H98, pp. 63-79 (1996).
Steidler et al., Science, Aug. 25, 2000, 289:1352-1355.
Steidler et al., Secretion of Biologically Active Murine Interleukin-2 by *Lactococcus lactis* subsp. lactis, Appl. Environ, Microbiol., 1995, 61:1627-1629.
Steidler et al., Therapeutic drug delivery by genetically modified *Lactococcus lactis*, Ann. N.Y. Acad. Sci., 2006, pp. 176-186, vol. 1072.
Steidler et al., "Treatment of Murine Colitis by *Lactococcus lactis* Secreting Interleukin-10," Science, Aug. 25, 2000, pp. 1352-1355, vol. 289.
Stern, et al., Microscopy Research and Technique, 2000, pp. 138-148, vol. 51.
Targan et al., Clarifying the causes of Croh's, 1995, Nature Medicine, pp. 1241-1243, vol. 1.
Taylor et al., Molecular Characterization of the Cell Cycle-regulated Thymidylate Synthase Gene of *Saccharomyces cerevisiae*, The Journal of Biological Chemistry, Apr. 15, 1987, pp. 5298-5307, vol. 262, No. 11.
Thompson et al., Plasmid, 2001, 46:188-201.
Un probiotique genetiquement modifie, Nature Biotechnology, on line, Jun. 15, 2003.
Vandenbrouke et al., Gastroenterology, pp. 502-513, vol. 127, Aug. 2004.
Van De Guchte et al., Applied and Environmental Microbiology, Jan. 1989, 55/1:224-228.
Van De Guchte et al., Heterologous Gene Expression in *Lactococcus lactis* subsp. lactis: Synthesis, Secretion, and Processing of the *Bacillus subtilis* Neutral Protease, Applied and Environmental Microbiology, Sep. 1990, p. 2606-2611, vol. 56. No. 9.
Van Mallaert et al., Med. Fac. Landbouww, Rijksuniv. Gent., 1989, 54(4b):1477-1485.
Verma et al., Gene therapy—promises: problems and prospects, 1997, Nature, pp. 239-242, vol. 389.
Waterfield et al., Gene, 1995, 165:9-15.
Wells et al., Applied & Environ. Microbiol., 59/11:3954-3959 (1993).
Wells et al., International Dairy Journal, 1995, 5:1071-1079.
Wells et al., Lactic acid bacteria as vaccine delivery vehicles, Antonie van Leeuwenhoek 70:317-330 (1996).
Wells et al., Molecular Microbiol. 8/6:1155-1162 (1993).
Wiedermann, Abstract, Prophylaxis and therapy of allergy by mucosal tolerance induction with recombinant allergens or allergen constructs, Current Drug Targets, Inflammation and Allergy, Oct. 1, 2005, pp. 577-583, vol. 4, No. 5, Bentham Science Publishers.
Williams et al., Plasmid, 2002, 47:241-245.
Willis, Bacterial drug delivery, Newsinbrief, online, Sep. 2003.

CD4⁺ SPLEEN (A)

(B)

(C)

(A)

(B)

TREATMENT OF IMMUNE DISEASE BY MUCOSAL DELIVERY OF ANTIGENTS USING GENETICALLY MODIFIED *LACTOBACILLUS*

CROSS-REFERENCE TO RELATED APPLICATION

This application is a divisional of U.S. patent application Ser. No. 12/448,921, filed Jul. 14, 2009, pending, the disclosure of which is hereby incorporated herein by this reference in its entirety.

TECHNICAL FIELD

The present invention relates to the treatment of autoimmune and allergic diseases by mucosal delivery by microorganisms, in particular *Lactococcus lactis*, of secreted immunodominant antigens.

FIELD OF THE INVENTION

The immune system has the task of distinguishing between self and non-self. The mucosal immune system, present along the respiratory, gastrointestinal and genitourinary tracts, has the additional burden of coexisting with an abundance of bacteria and innocuous antigens, such as food, airborne antigens or the commensally bacterial flora. A key feature of the mucosal immune system is its ability to remain tolerant to these antigens while retaining the capacity to repel pathogens effectively. Introduction of antigen systemically, whether by injection or injury, leads to local infiltration of inflammatory cells and specific immunoglobulin production. By contrast, antigens introduced at mucosal surfaces, such as the gastrointestinal and genitourinary tracts, elicit active inhibition of the immune response to those antigens systemically. The specific induction of these regulated responses by administration of antigen through the gastrointestinal tract is known as oral tolerance. Oral administration of antigen can lead to systemic unresponsiveness and is an attractive alternative to immunosuppressive medical inventions that have undesirable side-effects (such as steroids). The invention lies in particular in the field of low-dose tolerance, obtained by continued exposure to low doses of antigen. Tolerance inductions via the mucosa have been proposed as a treatment strategy against autoimmune, allergic and inflammatory diseases.

STATE OF THE ART

The following discussion of the background of the invention is merely provided to aid the reader in understanding the invention and is not admitted to describe or constitute prior art to the present invention.

Autoimmune, allergic and inflammatory diseases place a tremendous burden on the patient and society, resulting in decreased quality of life and huge costs. Moreover, no adequate treatment exists without acceptable side effects or which is socially appropriate. Current treatments for autoimmune disease are largely palliative, generally immunosuppressive, or anti-inflammatory. Non-immune therapies, such as hormone replacement in Hashimoto's thyroiditis or DM Type 1 treat outcomes of the autoaggressive response. Steroidal or NSAID treatment limits inflammatory symptoms of many diseases. IVIG is used for CIDP and GBS. More specific immunomodulatory therapies, such as the TNFα antagonists etanercept, have been shown to be useful in treating RA. Nevertheless, these immunotherapies may be associated with increased risk of adverse effects, such as increased susceptibility to infection. Celiac disease, which can be characterized by chronic small intestinal inflammation, can only be effectively treated by a socially restrictive diet that requires lifelong abstinence from foods that contain wheat, rye or barley. While a strict gluten free diet can lead to healing of the intestine the intolerance to gluten is permanent.

Celiac disease, also known as celiac sprue or gluten-sensitive enteropathy, is a chronic inflammatory disease that develops from an immune response to specific dietary grains that contain gluten. Diagnosis can be made based on the classical presentation of diarrhoea, fatty stools, abdominal bloating and cramping, weight loss, metabolic bone diseases, anaemia as well as the presence of serum antibodies with specificity for gliadin and tissue transglutaminase (tTG) (also termed anti-endomysial). The mucosal lesion is localized in the proximal part of the small intestine, and is characterized by villous atrophy, crypt cell hyperplasia, and lymphocytic infiltration of the epithelium and lamina propria, which release proinflammatory cytokines, such as IL-2 and IFN-γ, in response to gliadin. Celiac disease may be considered the most common food-sensitive enteropathy in humans, and may appear at any time in a person's life. The prevalence is in the range of 1:100 to 1:300 in Western, Arabian and Indian populations. Apart from gluten, the disease can be triggered for the first time after surgery, viral infection, severe emotional stress, pregnancy or childbirth.

Hence, induction of antigen specific oral tolerance would be an attractive therapeutic approach. Although oral tolerance was first described in 1911, it was not until the later 1970s that investigators started to address the mechanisms involved (Mayer and Shao, 2004a). Several mechanisms have been proposed for the development of oral tolerance, ranging from the deletion of anti-specific T-cells, over immune deviation and induction of anergy to suppression by Tregs (Mucida et al., 2005). Most investigators agree that there are two distinct ways of obtaining oral tolerance, the high-dose tolerance, obtained after a single high dose of antigen, which is based on anergy and/or deletion (Friedman and Weiner, 1994), and the low-dose tolerance, obtained by repeated exposure to low doses of antigen, mediated by active suppression of immune responses by $CD4^+$ T-cells, including $Foxp3^+$, IL-10 and/or TGF-β producing regulatory T-cells. Importantly, regulatory T cells induced through mucosal tolerance have been shown to mediate bystander suppression, a process through which regulatory cells specific for one protein suppress the response of nearby effector cells to another protein. Bystander suppression is a further important feature of antigen-induced suppression because the pool of antigens that induce organ-specific autoimmunity are largely unknown, and it overrides the phenomenon of epitope spreading. Epitope spreading is a complication of autoimmune and allergic diseases whereby the initiating immune response expands with time to include responses to other antigens.

Targeted and more efficient delivery of molecules for therapeutic and prophylactic applications is a priority for the pharmaceutical industry. Effective strategies should reduce the required dose, increase safety and improve efficacy by focusing molecules at the desired site of action. Mucosal routes of drug and vaccine delivery offer a number of logistical and biological advantages compared with injection. Oral delivery is particularly attractive as a result of the ease of administration. However, gastrointestinal degradation and low levels of absorption generally render this route of peptide and protein drug delivery ineffective. Alternative mucosal routes such as the nasal, rectal, pulmonary and ocular routes are also being investigated.

SUMMARY OF THE INVENTION

Surprisingly, we found that an immunodominant antigen which is delivered, and preferably continuously present, at a mucosal site of a patient induces an antigen-specific immunotolerance. In particular, when a micro-organism such as preferably *Lactococcus lactis* (LL), which constitutively expresses and secretes an immunodominant antigen, is delivered daily at a mucosal site, an antigen-specific immune tolerance was induced. We observed that the mucosal delivery of such an antigen by a *L. lactis* micro-organism gives a significantly better suppression of the antigen-specific immune response in comparison to the sole mucosal delivery of said antigen or said micro-organism.

We demonstrate that the invention can induce oral tolerance with much more higher efficiency than with monotherapy with antigen or control *L. lactis* alone. In vivo activation of antigen-specific regulatory T cells was strongly enhanced. Specifically, mucosal delivery of a gliadin derived peptide, which is immunodominant for DQ8 mediated T-cell responses by genetically modified *L. lactis*, induces suppression of local and systemic DQ8 restricted T-cell responses. Treatment resulted in an antigen-specific decrease of the proliferative capacity of the splenocytes and inguinal lymph node cells, which was critically dependent on the production of IL-10 and TGF-β and associated with a significant induction of Foxp3$^+$ regulatory T-cells. Because this approach of antigen-delivering bacteria has the capacity for potentiating oral tolerance even in the setting of established hypersensitivity, it is applicable for the treatment of celiac disease and other autoimmune and/or allergic diseases. The efficacy of the invention was demonstrated in autoimmune and allergic disease mouse models, as well as in the context of immune inactivation of therapeutics.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure to describe more fully the state of the art to which this invention pertains.

General Techniques

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular Cloning: A Laboratory Manual" Second Edition (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

Definitions

As used herein, certain terms may have the following defined meanings. As used in the specification and claims, the singular forms "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

Invention

We demonstrate that mucosal delivery of an immune dominant antigen secreted by a micro-organism such as preferably *L. lactis*, induces suppression of local and systemic T-cell responses. Treatment resulted in an antigen-specific decrease of the proliferative capacity of the splenocytes and inguinal lymph node cells, which was critically dependent on the production of IL-10 and TGF-β and associated with a significant induction of Foxp3$^+$ regulatory T-cells. This approach of antigen-delivering bacteria has the capacity for potentiating oral tolerance even in the setting of established hypersensitivity. Thus it is applicable for the treatment of celiac disease and other autoimmune and/or allergic diseases. The efficacy of the invention was demonstrated in autoimmune and allergic disease mouse models, as well as in the context of immune inactivation of therapeutics.

A first aspect of the invention is a method for inducing immune tolerance to an antigen, comprising mucosal delivery of said antigen by a micro-organism.

Preferably the invention relates to the use of a micro-organism, preferably a non-pathogenic micro-organism, more preferably lactic acid bacterium or yeast, even more preferably a *Lactococcus lactis* secreting an antigen for the preparation of a medicament, medical food or nutraceutical for mucosal delivery to treat an immune response related disease in a patient, wherein said antigen is preferably continuously present in said patient.

Preferably, said antigen is delivered by an antigen expressing micro-organism. Preferably said antigen is delivered by an antigen secreting or antigen displaying micro-organism or an intracellular antigen. Thus, the invention encompasses embodiments wherein said antigen is displayed at the surface of said antigen expressing micro-organism or wherein said antigen is secreted, or said antigen is freed upon digestion.

Preferably, the present invention relates to the use of an antigen expressing micro-organism for the preparation of a medicament for mucosal delivery to induce immune tolerance.

Preferably, said immune tolerance is induced in a patient. Said patient is preferably an animal. Said animal is preferably a mammal, and preferably chosen from the group consisting of mouse, rat, pig, cow, sheep, horses and human. Preferably, said mammal is human. Preferably, said immune tolerance is mucosal tolerance.

Mucosa

Mucosa as used here can be any mucosa such as oral mucosa, rectal mucosa, urethral mucosa, vaginal mucosa, ocular mucosa, buccal mucosa, pulmonary mucosa and nasal mucosa. Mucosal delivery as used throughout the application encompasses the delivery to the mucosa. Oral mucosal delivery includes buccal, sublingual and gingival routes of delivery. Accordingly, the present invention relates to method in which said mucosal delivery is chosen from the group consisting of rectal delivery, buccal delivery, pulmonary delivery, ocular delivery, nasal delivery, vaginal delivery and oral delivery. Preferably, said mucosal delivery is oral delivery and said tolerance is oral tolerance.

Mucosal tolerance as used here throughout the application is the inhibition of specific immune responsiveness to an antigen in an animal (including humans), after that said animal has been exposed to said antigen via the mucosal route. Preferably, said mucosal tolerance is systemic tolerance. The subsequent exposure of the antigen can be every exposure known to the person skilled in the art, such as exposure by parenteral injection, by mucosal delivery, or by endogenous production such as in the case of auto-antigens. Oral tolerance is the inhibition of specific immune responsiveness to an antigen in an animal (including humans), after that said animal has been exposed to said antigen via the oral route. Low dose oral tolerance is oral tolerance induced by low doses of antigens, and is characterized by active immune suppression, mediated by cyclophosphamide sensitive regulatory T-cells that can transfer tolerance to naïve hosts. High dose oral tolerance is oral tolerance induced by high doses of antigens, is insensitive to cyclophosphamide treatment, and proceeds to induction of T cell hyporesponsiveness via anergy and/or deletion of antigen specific T-cells. The difference in sensitivity to cyclophosphamide can be used to make a distinction between low dose and high dose tolerance (Strobel et al., 1983). Preferably, said oral tolerance is low dose oral tolerance as described by Mayer and Shao (2004b).

The present invention thus relates to a method or use as described herein, wherein said induction of immune tolerance is at least 1.5, preferably 2, more preferably 3 times or more relative to before said induction. Alternatively, said antigen is tolerated at least 1.5, 2, 3 times or more relative to before said induction. The induction of immune tolerance can be measured by methods known in the art. Preferably, said induction of immune tolerance can be measured by modulation of a cytokine level in said animal. As such, the modulation can be an increase of a cytokine level, for instance said increase of a cytokine level is at least 1.5, 2, 3 times or more relative to before said induction, e.g., IL-10 or TGF-β. Alternatively, said modulation is a decrease of the level of a particular cytokine level, for instance said decrease of the cytokine level is at least 1.5, 2, 3 times or more relative to before said induction, e.g., IL-12, IL-17 and IFN-γ. The cytokines which are modulated may be chosen from any relevant cytokines, preferably said cytokines are chosen from the group consisting of IL-2, IL-4, IL-5, IL-6, IL-10, IL-12, IL-13, IL-17, IL-23, TNF-α, IFN-γ, IFN-α, MCP-1, TGF-β, RANK-L and Flt3L.

Constructs, Delivery & Integration

In the present invention, the micro-organism delivers the antigen at the intended site, i.e., mucosa. The micro-organism expresses said antigen, after which the antigen is exposed on the cell surface or secreted. Hence, in a preferred embodiment the micro-organism, such as L. lactis, comprises an expression vector capable of expressing the heterologous antigen, e.g., the antigen used for inducing immune tolerance, intracellularly, secreted and/or such that the heterologous antigen is exposed on the cell surface under conditions present at the intended mucosa, e.g., such as in the gastrointestinal tract. The micro-organism, e.g., L. lactis, can comprise expression vectors capable of expressing the heterologous antigen intracellularly, secreted and/or such that the heterologous antigen is exposed on the cell surface to a degree sufficient to induce immune tolerance. As high a degree of expression as possible without damaging the viability of the cell or the host to be treated is envisaged. With higher expression, less frequent and lower doses may be required for tolerance purposes. Naturally the dosage regime will not only depend on amount of antigen but also on antigen type and the presence or absence of other immunogenicity stimulating or suppressing factors in the composition.

Usually, the expression system will comprise a genetic construct comprising at least one nucleotide sequence encoding the desired antigen, preferably operably linked to a promoter capable of directing expression of the sequence in the hosting micro-organism. Suitably the antigen to be expressed can be encoded by a nucleic acid sequence that is adapted to the preferred codon usage of the host. The construct may further contain (all) other suitable element(s), including enhancers, transcription initiation sequences, signal sequences, reporter genes, transcription termination sequences, etc., operable in the selected host, as is known to the person skilled in the art. The construct is preferably in a form suitable for transformation of the host and/or in a form that can be stably maintained in the host, such as a vector, plasmid or mini-chromosome. Suitable vectors comprising nucleic acid for introduction into micro-organisms, e.g., bacteria, can be chosen or constructed, containing appropriate regulatory sequences, including promoter sequences, terminator fragments, enhancer sequences, marker genes and other sequences as appropriate. Vectors may be plasmids, viral e.g., 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al., eds., John Wiley & Sons, 1992. The disclosures of Sambrook et al., and Ausubel et al., are incorporated herein by reference. In a preferred embodiment, the coding sequences for the biologically active polypeptide and the antigen are contained in an operon, i.e., a nucleic acid construct for multi-cistronic expression. In an operon, transcription from the promoter results in a mRNA which comprises more than one coding sequence, each with its own suitably positioned ribosome binding site upstream. Thus, more than one polypeptide can be translated from a single mRNA. Use of an operon enables expression of the biologically active polypeptide and the antigen to be co-ordinated. More preferably, a food grade construct is used.

In an embodiment the present invention relates to stably transfected micro-organisms, i.e., micro-organisms in which the gene coding for the antigen has been integrated into the host's genome. Techniques for establishing stably transfected micro-organisms are known in the art. For instance, the gene of interest may be cloned into the host's genome via homologous recombination. Preferably, an essential gene of the host is disrupted by the homologous recombination event, such as deletion of the gene, one or more amino acid substitutions leading to an inactive form of the protein encoded by the essential gene, or to a frameshift mutation resulting in a truncated form of the protein encoded by the essential gene. In an embodiment, the essential gene is the thyA gene. A preferred technique is described in WO02/090551, which is specifically incorporated herein in its entirety. The transforming plasmid can be any plasmid, as long as it cannot complement the disrupted essential gene, e.g., thyA gene. The plasmid may be a self-replicating, preferably carrying one or more genes of interest and one or more resistance markers, or the plasmid is an integrative plasmid. In the latter case, the integrative plasmid itself may be used to disrupt the essential gene, by causing integration at the locus of the essential gene, e.g., thyA site, because of which the function of the essential gene, e.g., the thyA gene, is disrupted. Preferably, the essential gene, such as the thyA gene, is replaced by double homologous recombination by a cassette comprising the gene or genes of interest, flanked by targeting sequences that target the insertion to the essential gene, such as the thyA target site. It will be appreciated that that these targeting sequences are sufficiently long and sufficiently homologous to enable integration of the gene of interest into the target site.

The genetic construct encoding the antigen of the invention may thus be present in the host cell extra-chromosomally, preferably autonomously replicating using an own origin of replication, or may be integrated into the microbial genomic DNA, e.g., bacterial or yeast chromosome, e.g., *Lactococcus* chromosome. In the latter case, a single or multiple copies of the said nucleic acid may be integrated; the integration may occur at a random site of the chromosome or, as described above, at a predetermined site thereof, preferably at a predetermined site, such as, in a preferred non-limiting example, in the thyA locus of *Lactococcus*, e.g., *Lactococcus lactis*.

Hence, in an embodiment, the genetic construct encoding the antigen of the invention may further comprises sequences configured to effect insertion of the said genetic construct into the genome, e.g., a chromosome, of a host cell.

In an example, insertion of the genetic construct into particular sites within a genome, e.g., chromosome, of a host cell may be facilitated by homologous recombination. For instance, the genetic construct the invention may comprise one or more regions of homology to the said site of integration within the genome e.g., a chromosome, of the host cell. The sequence at the said genome, e.g., chromosome, site may be natural, i.e., as occurring in nature, or may be an exogenous sequence introduced by previous genetic engineering.

For instance, the said region(s) of homology may be at least 50 bp, preferably at least 100 bp, e.g., at least 200 bp, more preferably at least 300 bp, e.g., at least 400 bp, even more preferably at least 500 bp, e.g., at least 600 bp or at least 700 bp, still more preferably at least 800 bp, e.g., at least 900 bp, or at least 1000 bp or more.

In a preferred example, two regions of homology may be included, one flanking each side of the relevant expression units present in the genetic construct of the invention. Such configuration may advantageously insert the relevant sequences, i.e., at least the ones encoding and effecting the expression of the antigen of interest, in host cells. Ways of performing homologous recombination, especially in bacterial hosts, and selecting for recombinants, are generally known in the art.

Transformation methods of micro-organisms are known to the person skilled in the art, such as for instance protoplast transformation and electroporation.

A high degree of expression can be achieved by using homologous expression and/or secretion signals on the expression vectors present in the micro-organism, e.g., *L. lactis*. Suitably expression regulating signals as present in the constructs in the Examples are useful. Other expression signals will be apparent to the person skilled in the art. The expression vector can be optimised for expression depending on the micro-organism, e.g., *L. lactis*, it is incorporated in. For instance, specific expression vectors that gave sufficient levels of expression in *Lactococcus, Lactobacillus lactis, casei* and *plantarum* are known. Moreover, systems are known which have been developed for the expression of heterologous antigens in the non-pathogenic, non-colonising, non-invasive food-grade bacterium *Lactococcus lactis* (see UK patent GB2278358B, which is incorporated herein by reference). A particularly preferred construct according to the invention comprises the multi-copy expression vector described in PCT/NL95/00135 (WO-A-96/32487), in which the nucleotide sequence encoding the antigen has been incorporated. Such a construct is particularly suitable for expression of a desired antigen in a lactic acid bacterium, in particular in a *Lactobacillus*, at a high level of expression, and also can be used advantageously to direct the expressed product to the surface of the bacterial cell. The constructs (e.g., of PCT/NL95/00135) may be characterised in that the nucleic acid sequence encoding the antigen is preceded by a 5' non-translated nucleic acid sequence comprising at least the minimal sequence required for ribosome recognition and RNA stabilisation. This can be followed by a translation initiation codon which may be (immediately) followed by a fragment of at least 5 codons of the 5' terminal part of the translated nucleic acid sequence of a gene of a lactic acid bacterium or a structural or functional equivalent of the fragment. The fragment may also be controlled by the promoter. The contents of PCT/NL95/00135, including the differing embodiments disclosed therein, and all other documents mentioned in this specification, are incorporated herein by reference. One aspect of the present invention provides a method which permits the high level regulated expression of heterologous genes in the host and the coupling of expression to secretion. In a further preferred embodiment, the T7 bacteriophage RNA polymerase and its cognate promoter are used to develop a powerful expression system according to WO93/17117, which is incorporated herein by reference. Preferably the expression plasmid is derived from pT1 NX.

A promoter employed in accordance with the present invention is preferably expressed constitutively in the bacterium. The inventors observed that constitutive expression of the antigen resulted in increased immune tolerance in contrast to inducible expression. Furthermore, the use of a constitutive promoter avoids the need to supply an inducer or other regulatory signal for expression to take place. Preferably, the promoter directs expression at a level at which the bacterial host cell remains viable, i.e., retains some metabolic activity, even if growth is not maintained. Advantageously then, such expression may be at a low level. For example, where the expression product accumulates intracellularly, the level of expression may lead to accumulation of the expression product at less than about 10% of cellular protein, preferably about or less than about 5%, for example about 1-3%. The promoter may be homologous to the bacterium employed, i.e., one found in that bacterium in nature. For example, a Lactococcal promoter may be used in a *Lactococcus*. A preferred promoter for use in *Lactococcus lactis* (or other Lactococci) is "P1" derived from the chromosome of *Lactococcus lactis* (Waterfield, N R, Lepage, R W F, Wilson, P W, et al. (1995). The isolation of lactococcal promoters and their use in investigating bacterial luciferase synthesis in *Lactococcus lactis*. *Gene* 165(1), 9-15). Another preferred promoter is the usp45 promoter.

The nucleic acid construct or constructs may comprise a secretory signal sequence. Thus, in a preferred embodiment the nucleic acid encoding an antigen may provide for secretion of said antigen (by appropriately coupling a nucleic acid sequence encoding a single sequence to the nucleic acid sequence encoding the antigen). Ability of a bacterium harbouring the nucleic acid to secrete the antigen may be tested in vitro in culture conditions which maintain viability of the organism. Preferred secretory signal sequences include any of those with activity in Gram positive organisms such as *Bacillus, Clostridium* and *Lactobacillus*. Such sequences may include the α-amylase secretion leader of *Bacillus amyloliquetaciens* or the secretion leader of the Staphylokinase enzyme secreted by some strains of *Staphylococcus*, which is known to function in both Gram-positive and Gram-negative hosts (see "Gene Expression Using *Bacillus*," Rapoport (1990) Current Opinion in Biotechnology 1:21-27), or leader sequences from numerous other *Bacillus* enzymes or S-layer proteins (see pp 341-344 of Harwood and Cutting, "Molecular Biological Methods for *Bacillus*," John Wiley & Co. 1990). Preferably, said secretion signal is derived from usp45 (Van Asseldonk et al., 1993 Mol. Gen. Genet. 240:428-434). Preferably, said antigen is constitutively secreted.

In an alternative embodiment, the coding sequences for the biologically active polypeptide and the antigen are part of the same nucleic acid vector, or separate vectors, and are individually under the regulatory control of separate promoters. The promoters may be the same or different. A nucleic acid construct or vector comprising a coding sequence for a biologically active polypeptide and a coding sequence for an antigen wherein each coding sequence is under the control of a promoter for expression in a non-invasive host, e.g., *Lactococcus*, whether as an operon or not, is provided by a further aspect of the present invention.

Antigens

The sequence encoding the antigen can be obtained from any natural source and/or can be prepared synthetically using well known DNA synthesis techniques. The sequence encoding the antigen can then (for instance) be incorporated in a suitable expression vector to provide a genetic construct of the invention, which is then used to transform or transfect the intended host. The recombinant thus obtained can then be cultured, upon which the harvested cells can be used to formulate the composition, optionally after further purification and/or processing steps, such as freeze-drying to form a powder.

An antigen can be any antigen known to the person skilled in the art. An antigen as used here throughout the application is preferably any substance that provokes an immune response when introduced in the body of an animal, wherein said immune response can be T-cell mediated and/or a B-cell mediated response. The antigen may comprise a T-cell epitope and/or a B-cell epitope. The length of the antigen is not particularly limiting, provided said antigen can be expressed in the micro-organism of the invention. The antigen can be a protein or a part thereof, such as a polypeptide or a peptide. The antigens according to the invention include linear and/or conformational epitopes. T-cell mediated responses cover Th1, Th2 and/or Th17 responses. The antigen can be any antigen, such as, but not limited to allergens (including food allergens), allo-antigens, self-antigens, autoantigens, and therapeutic molecules or antigens that induce an immune response. Preferably, said antigen is involved in the induction of immune response related diseases. Even more preferably, said antigen is involved in the induction of allergic asthma, multiple sclerosis, type 1 diabetes, autoimmune uveitis, autoimmune thyroiditis, autoimmune myasthenia gravis, rheumatoid arthritis, food allergy, celiac disease or graft versus host disease.

The inventors observed that the secreted immunodominant antigens of the invention suppress systemic inflammatory T-cell responses, and that these antigens are necessary and sufficient for the induction of a significant tolerogenic effect.

Regulatory T cells (Treg) play a critical role in the induction and maintenance of oral tolerance. Induction of Treg is a major goal for immunotherapy for several autoimmune, allergic and inflammatory diseases. Current strategies for therapeutic induction of antigen-specific suppressor cells face significant hurdles, and usually require strenuous techniques to isolate, handle and transfer adequate numbers of regulatory cells. The micro-organism, e.g., *L. lactis*-antigen delivery system of the present invention circumvents these problems and effectively induces antigen-specific Treg. In the present invention it was demonstrated that induction of Treg can be achieved by exposing the mucosal immune system to low doses of antigen. The exposure to low doses of antigen is preferably a continued exposure. Hence, the present invention relates to antigens inducing and/or expanding Treg cells, preferably $CD4^+CD25^+$, $CD4^+CD25^-$ and $CD8^+$ Treg cells.

It was further demonstrated in the present invention that the Treg cells which were induced and/or expanded by the antigens according to the invention function through a TGF-β and/or IL-10 dependent mechanism. Previously evidence has been provided that TGF-β plays a critical role in oral tolerance as well as in the development of peripheral induced Treg. Accordingly, the present invention provides immunodominant antigens which stimulate endogenous TGF-β and/or IL-10 expression.

Moreover, it was shown that antigen-specific TGF-β producing Th3 cells drive the differentiation of antigen-specific $Foxp3^+$ regulatory cells in the periphery. Furthermore TGF-β dependent conversion of peripheral $CD4^+CD25^-$ T cells into $CD25^+$, $CD45RB^-$/low suppressor cells has been reported. It was shown that oral tolerance induced by CTB-conjugated Ag is associated with increase in TGF-β by the generation of both $Foxp3^+CD25^+$and both $Foxp3^+$ and $Foxp3-CD25^-$ $CD4^+$ regulatory T Cells. These data suggest a key role for $Foxp3^+$ 'adaptive' Treg in the induction and maintenance of oral tolerance. We also show a significant mucosal Foxp3 induction. Moreover, the 'mucosal' induced regulatory T-cell tends to be antigen specific as *L. lactis* alone is unable to induce this Foxp3 upregulation within the GALT. Accordingly, the present invention relates preferably to $Foxp3^+$ Treg cells.

The present invention further demonstrated that the Treg cells which were induced and/or expanded by the antigens according to the invention decreased inflammation, in particular in the spleen and inguinal lymph node cells. Moreover, the IFN-γ and IL-12 production was decreased. Accordingly, the present invention provides immunodominant antigens which decrease endogenous IFN-γ and/or IL-12 production, and/or stimulate endogenous TGF-β and/or IL-10 expression. Moreover, the present invention relates to antigens reducing proliferation of spleen and/or inguinal lymph node cells. It will be appreciated that the present invention relates also to antigens suppressing inflammatory antigen specific T cell response.

It will be appreciated that certain HLA-DQ isoforms are more commonly associated with certain autoimmune diseases. For instance, the chronic small intestinal inflammation that defines celiac disease is characterized by a loss of tolerance to ingested gluten peptides and is strongly associated with a HLA-DQ2 or HLA-DQ8 restricted T-cell response. The expression of HLA-DQ2 or HLA-DQ8 is necessary for the expression of celiac, and confer up to 40% of the genetic risk in Western populations. One of the most important aspects in the pathogenesis of celiac is the activation of a T-helper 1 immune response, which arises when antigen-presenting cells that express HLA-DQ2/DQ8 molecules present gluten peptides to CD4+ T-cells.

DQ8 stands out because of its strong association with not only celiac disease but also juvenile diabetes. It is also linked to HLA-DR alleles that are implicated in RA and may increase risk. HLA-DQ is not spread uniformly and certain populations are at increased risk; however that risk is often dependent on environment (gluten consumption) and increasing prevalence of some diseases may be the result of shifts of individual from low-risk environments to higher risk environments.

The HLA DQ8 according to the invention is the serotypic representation of an DQA1:DQB1 haplotype. DQ8 represents the haplotypes DQA1*0301:DQB1*0302, DQA1*0302:DQB1*0302, or DQA1*0303:DQB1*0302 haplotypes. These haplotypes are associated with some of the most common autoimmune disease known. DQA1*0301: DQB1*0302 is the most frequent of these 3 haplotypes and represents about 80% of the global DQ8. The present invention thus relates to antigens recognized via DQA1*0301: DQB1*0302, DQA1*0302:DQB1*0302, and/or DQA1*0303:DQB1*0302 haplotypes, referred to as "DQ8 epitope."

HLA-DQ2 is expressed in more than 90% of people with celiac disease. HLA DR3-DQ2 is the serotypic representation of a HLA-DRB1: DQA1:DQB1 haplotype. DR3-DQ2 principally represents the haplotype DRB1*0301: DQA1*0501: DQB1*0201. It is relatively abundant in western hemisphere. DQ2 is encoded by DQB1*02 alleles in combination with other alpha alleles. The two most common DQ2 β chains are very similar. The present invention thus relates to antigens recognized via DQB1*0201, DQB1*0202 and/or DQB1*0203 haplotypes, referred to as "DQ2 epitope."

The present invention relates preferably to antigens which are derived from glycoproteins. Preferably said antigens are derived from gliadin, preferably α-gliadin and/or hordein. The gliadins, which can be subdivided into the α-, γ-, and .omega.-gliadins, and hordein are well known in the art, and their sequences are easily retrievable via public domain libraries, such as NCBI. Preferably, said α-gliadin is derived from *Triticum*, such as *T. aestivum* or *T. turgidum*.

The present invention demonstrates that CD4+ T cells recognize native gluten peptides in the context of DQ2 or DQ8.

In an embodiment the present invention relates to the DQ8 epitope: QYPSGQGSFQPSQQNPQA, corresponding to residues 203-220 of the sequence retrievable via UniProtKB/ TrEMBL entry Q9M4L6 (SEQ ID NO: 4).

Said native DQ8 epitope is preferably encoded by the nucleotide sequence 5'-caa tac cca tca ggt caa ggt tca ttc caa cca tca caa caa aac cca caa get-3'. (SEQ ID NO: 3)

In an embodiment the present invention relates to the DQ2 epitope: LQLQPF-PQPQLPYPQPQLPYPQPQLPYPQPQPF, corresponding to residues 57-89 of the sequence retrievable via UniProtKB/ TrEMBL entry Q9M4L6 (SEQ ID NO: 8)

Said DQ2 epitope is preferably encoded by the nucleotide sequence 5'-tta caa tta caa cca ttc cca caa cca caa tta cca tac cca tta cca tac cca caa cca caa tta cca tac cca caa cca caa cca ttc (SEQ ID NO: 7)

Antigens are commonly deamidated in the intestines by e.g., endogenous tissue trans-glutaminase. Deamidated antigens are more immune reactive and readily recognized than antigens which are not deamidated. The presence of endogenous tissue trans-glutaminase is indifferent in case the antigens are deamidated by other means. In an embodiment, the present invention relates to deamidated antigens, encoded by nucleotide sequences in which codons for glutamine residues in epitopes are preferably replaced by codons for glutamic acid residues.

In particular, the present invention relates to deamidated DQ8 epitope QYPSGEGSFQPSQENPQA. (SEQ ID NO: 2)

Said deamidated DQ8 epitope is preferably encoded by the nucleotide sequence 5'-caa tac cca tca ggt gaa ggt tca ttc caa cca tca caa gaa aac cca caa get-3'. (SEQ ID NO: 1)

In particular, the present invention relates to deamidated DQ2 epitope LQL QPF PQP ELP YPQ PQL PYP QPE LPY PQP QPF (SEQ ID NO: 6)

Said deamidated DQ2 epitope is preferably encoded by the nucleotide sequence 5'-tta caa tta caa cca ttc cca caa cca gaa tta cca tac cca tta cca tac cca caa cca gaa tta cca tac cca caa cca caa cca ttc (SEQ ID NO: 5)

It was further demonstrated that the presence of additional sequences, such as a tag, to the epitope sequences did not influence the immune response. Accordingly, in further embodiments, said epitope may comprise further amino acids, such as for instance 50 amino acids, 43, 30, 25, 20, 19, 18, 17, 16, 15, 14, 13, 12, 11, 10, 9, 8, 7, 6, 5, 4, 3, 2, or 1 amino acid(s). Hence, the present invention relates to DQ8 epitopes comprising at most 50 additional amino acids. In a further embodiment, the present invention relates to the amino acid sequence GAPVPYPDPLEPRQYPSGEGSFQPSQENPQA (SEQ ID NO: 16), comprising a DQ8 epitope and an e-tag (GAPVPYPDPLEPR (SEQ ID NO: 31)).

Immune Response

An immune response related disease as used here is a disease caused by an unwanted immune response of the body against an antigen, whereby said antigen can be either a heterologous antigen or an auto-antigen. Immune response related diseases include, but are not limited to allergic reaction including food allergy, celiac disease, allergic asthma, autoimmune uveitis, autoimmune thyroiditis, autoimmune myasthenia gravis, rheumatoid arthritis, type 1 diabetes and multiple sclerosis. Immune response related diseases also include unwanted immune reactions such as graft versus host disease or immune activation of medication such as the antibody production against non endogenous Factor VIII. Preferably, the disease is selected from the group consisting of allergic asthma, food allergy, celiac disease, type 1 diabetes and immune inactivation of therapeutics. It will thus be appreciated that immune response related diseases include, but are not limited to allergic reaction including food allergy, celiac disease, allergic asthma, autoimmune uveitis, autoimmune thyroiditis, autoimmune myasthenia gravis, rheumatoid arthritis, type 1 diabetes and multiple sclerosis. Immune response related diseases also include unwanted immune reactions such as graft versus host disease or immune-activation of medication such as the antibody production against non endogenous Factor VIII. Preferably, the disease is selected from the group consisting of allergic asthma, food allergy, celiac disease, graft versus host disease, type 1 diabetes and immune inactivation of therapeutics.

According to the present invention the term "immunodominant" relates to the principle antigens inducing an immune response.

In view of the above, it will thus be appreciated that the present invention relates to method or use as described herein, wherein said method or use is therapeutic and/or prophylactic.

A further aspect of the invention relates to a method for inducing immune tolerance to an antigen, comprising mucosal delivery of said antigen by a micro-organism in combination with mucosal delivery of an immune-modulating compound producing micro-organism. The immune-modulating compound and the antigen may be delivered by the same micro-organism, or it may be a different micro-organism.

Medicament and Administration

Compound means any chemical of biological compound or complex, including simple or complex organic and inorganic molecules, peptides, peptido-mimetics, proteins, protein complexes, antibodies, carbohydrates, nucleic acids or derivatives thereof. An immune-modulating compound is a compound that modifies the function of the immune system. An immune-modulating compound as used here is a tolerance inducing compound; tolerance induction can be obtained, as a non-limiting example, in a direct way by inducing regulatory T-cells such as Treg, Trl or Th3, or by shifting the Th1/Th2 balance towards Th1 or Th2, or by inhibiting Th17, or in an indirect way, by activation of immature dendritic cells to tolerizing dendritic cells and/or inhibiting Th2 immune response inducing expression of "co-stimulation" factors on mature dendritic cells. Immune-modulating and immune-suppressing compounds are known to the person skilled in the art and include, but are not limited to bacterial metabolites such as spergualin, fungal and streptomycal metabolites such as tacrolimus, rapamicin or ciclosporin, immune-suppressing cytokines such as IL-4, IL-10, IFN$\alpha$ TGF-$\beta$ (as selective adjuvant for regulatory T-cells) Flt3L, TSLP, CTB and Rank-L (as selective tolerogenic DC inducers antibodies and/or antagonist such as anti-CD40L, anti-CD25, anti-CD20, anti-IgE, anti-CD3, anti-IL-6 (or IL6R) and proteins, peptides or fusion proteins such as the CTL-4 Ig or CTLA-4 agonist fusion protein.

Thus, the immune-modulating compound can be any immune-modulating compound known to the person skilled in the art. Preferably, said immune-modulating compound is an immune-suppressing compound, even more preferably said compound is an immune-suppressing cytokine or antibody. Preferably, said immune-suppressing cytokine is a tolerance-enhancing cytokine or antibody. Immune-suppressing cytokines are known to the person skilled in the art, and include, but are not limited to IL-4, IL-10, IFN-$\alpha$ and TGF-$\beta$, as selective adjuvant for regulatory T-cells; and Flt3L, TSLP, CTB and Rank-L, as selective tolerogenic DC inducers. Preferably, said immune-suppressing cytokine is selected from the group consisting of IL-4, IL-10, IFN$\alpha$ and Flt3L. It will be appreciated by the person skilled in the art that the present invention also relates to functional homologues thereof. A functional homologue connotes a molecule having essentially the same or similar, at least for the intended purposes, function, but can differ structurally. Most preferably, said immune-suppressing tolerance-enhancing cytokine is IL-10, or a functional homologue thereof. Preferably, said immune-suppressing antibody is chosen from the group consisting of anti-IL-2, anti-IL12, anti-IL6, anti-IFN-$\gamma$.

Delivery as used here means any method of delivery known to the person skilled in the art and includes, but is not limited to, coated or non-coated pharmaceutical formulations of the compound to deliver, capsules, liposomes, oil bodies, polymer particles comprising or carrying the compound to deliver or micro-organisms secreting, displaying or accumulating the compound to deliver, optionally in presence of compounds that may enhance mucosal delivery and/or mucosal uptake.

Compounds or compositions described herein may be administered in pure form, combined with other active ingredients, or combined with pharmaceutically acceptable non-toxic excipients or carriers. Oral compositions will generally include an inert diluent carrier or an edible carrier. Pharmaceutically compatible binding agents, and/or adjuvant materials can be included as part of the composition. Tablets, pills, capsules, troches, enema and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as fatty oil. In addition, dosage unit forms can contain various other materials that modify the physical form of the dosage unit, for example, coatings of sugar, shellac, or enteric agents. Further, syrup may contain, in addition to the active compounds, sucrose as a sweetening agent and certain preservatives, dyes, colorings, and flavorings. It will be appreciated that the form and character of the pharmaceutically acceptable carrier is dictated by the amount of active ingredient with which it is to be combined, the route of administration and other well-known variables. The carrier(s) must be "acceptable" in the sense of being compatible with the other ingredients of the formulation and not deleterious to the recipient thereof.

Alternative preparations for administration include sterile aqueous or nonaqueous solutions, suspensions, and emulsions. Examples of non-aqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Various liquid formulations are possible for these delivery methods, including saline, alcohol, DMSO, and water based solutions.

Preferably said antigen and/or said immune-suppressing cytokine is expressed in low amounts, preferably 0.1 µg or lower per dose bacteria administered in a mice experimental setting, such amounts to be translated in a human disease setting.

The terms "treatment," "treating," and the like, as used herein include amelioration or elimination of a developed mental disease or condition once it has been established or alleviation of the characteristic symptoms of such disease or condition. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. It should be clear that mental conditions may be responsible for physical complaints. In this respect, the term "treating" also includes prevention of a physical disease or condition or amelioration or elimination of the developed physical disease or condition once it has been established or alleviation of the characteristic symptoms of such conditions.

As used herein, the term "medicament" also encompasses the terms "drug," "therapeutic," "potion" or other terms which are used in the field of medicine to indicate a preparation with therapeutic or prophylactic effect.

It will be appreciated that the compound of the invention, i.e., the antigen, is delivered or expressed in a therapeutically effective amount. As used herein, the term "therapeutically effective amount" is meant to refer to an amount of a compound or composition of the present invention that will elicit a desired therapeutic or prophylactic effect or response when administered according to the desired treatment regimen. It is observed that when the immune-dominant antigen is continuously present, the inflammatory antigen specific cell response is even reduced further. This reduction is significantly larger compared to administration of the antigen as such, the micro-organism as such, or the non-continuous presence of the antigen. The term "continuously present" or "continued presence" according to the invention relates to the constant or uninterrupted presence of an antigen according to invention at the intended mucosal site, e.g., the site of inflammation. The presence of the antigen can be measured by techniques well known in the art, such as PCR, ELISA or immune precipitation techniques, such as for instance detailed in the examples section and supra. Moreover, the presence of *L. lactis* may be a measure of the presence of the antigen. Also, the effects caused by the antigen may be a measure of the presence of the antigen, such as, for instance, the presence or increase of endogenous TGF-β or IL-10 levels, or a decrease of IFN-γ or IL-12 levels, or the presence of Treg cells, such as described herein, or a decrease of the proliferative capacity of the splenocytes and draining lymph node cells. It will thus be appreciated that the levels of the antigen may vary, while the antigen is still considered to be continuously present.

Preferably the compound or composition is provided in a unit dosage form, for example a tablet, capsule, enema or metered aerosol dose, so that a single dose is administered to the subject, e.g., a patient.

The active ingredients may be administered from 1 to 6 times a day, sufficient to exhibit the desired activity. These daily doses can be given as a single dose once daily, or can be given as two or more smaller doses at the same or different times of the day which in total give the specified daily dose. Preferably, the active ingredient is administered once or twice a day. For instance, one dose could be taken in the morning and one later in the day.

In all aspects of the invention, the daily maintenance dose can be given for a period clinically desirable in the patient, for example from 1 day up to several years (e.g., for the mammal's entire remaining life); for example from about (2 or 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Other constituents of the liquid formulations may include preservatives, inorganic salts, acids, bases, buffers, nutrients, vitamins, or other pharmaceuticals.

The micro-organism delivering the antigen may be delivered in a dose of at least $10^4$ colony forming units (cfu) to $10^{12}$ cfu per day, preferably between $10^6$ cfu to $10^{12}$ cfu per day, most preferably between $10^9$ cfu and $10^{12}$ cfu per day. In accordance with the method as described in Steidler et al. (Science 2000), the antigen and possibly the immuno-modulating compound of e.g., of $10^9$ cfu is secreted to at least 1 ng to 100 ng. Through ELISA, known to a person skilled in the art, the skilled person in the art can calculate the range of secretion of antigen in relation to any other dose of cfu.

The antigen may be delivered in a dose inducing a low-dose response. Preferably, said antigen is delivered in a dose of at least 10 fg to 500 µg per day, preferably between 1 pg and 250 µg per day, more preferably between 100 pg and 200 µg per day, or preferably 1 ng and 150 µg, or more preferably 10 ng and 125 µg per day, even more preferably 100 ng and 100 µg per day, even more preferably 1 µg and 90 µg per day and most preferably between 10 µg and 75 µg per day, such as, for instance, 25 µg, 30 µg, 40 µg, 50 µg, 60 µg or 70 µg per day.

Preferably the compounds or composition is provided in a unit dosage form, for example a tablet, solution, capsule or metered aerosol dose, so that a single dose is administered to the subject, e.g., a patient.

Depending on the mode of administration, e.g., oral, or any of the ones described above, the man skilled in the art knows how to define or calculate the actual dose to be administered to a patient. The person skilled in the art will be knowledgeable to adjust the doses depending on the patient, micro-organism, vector et cetera.

Compounds of the present invention also may take the form of a pharmacologically acceptable salt, hydrate, solvate, or metabolite. Pharmacologically acceptable salts include basic salts of inorganic and organic acids, including but not limited to hydrochloric acid, hydrobromic acid, sulphuric acid, phosphoric acid, nitric acid, methanesulphonic acid, ethanesulfonic acid, p-toluenesulfonic acid, naphtalenesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function, such as a carboxy group, then suitable pharmaceutically acceptable cation pairs for the carboxy group are well known to those skilled in the art and include alkaline, alkaline earth, ammonium, quaternary ammonium cations and the like.

Micro-Organism

The micro-organism according to the invention can be any micro-organism, including bacteria, yeasts or fungi, suitable for mucosal delivery. Preferably, said micro-organism is a non pathogenic micro-organism, even more preferably said micro-organism is a probiotic micro-organism. Probiotic organisms are known to the person skilled in the art. Probiotic organisms include, but are not limited to, bacteria such as *Lactobacillus* sp., *Lactococcus* sp. and yeasts such as *Saccharomyces cerevisiae* subspecies *boulardii*. Preferably, said bacterium is a lactic acid bacterium. Even more preferably, said lactic acid bacterium is chosen from the group consisting of *Lactobacillus, Leuconostoc, Pediococcus, Lactococcus, Streptococcus, Aerococcus, Carnobacterium, Enterococcus, Oenococcus, Teragenococcus, Vagococcus,* and *Weisella*. In one further preferred embodiment, said micro-organism is *Lactococcus lactis*. In another preferred embodiment said lactic acid bacterium is a *Lactobacillus* sp. In another preferred embodiment, said micro-organism is *Saccharomyces cerevisiae*, even more preferably said yeast is *Saccharomyces cerevisiae* subsp. *Boulardii*.

Most preferably said probiotic micro-organism is a lactic acid bacterium, as delivery of heterologous proteins (i.e., non Lactic acid bacterial proteins) by lactic acid bacteria into the mucosa, including both oral and vaginal delivery, has been described (Steidler and Rottiers, 2006; Liu et al., 2006), which makes these lactic acid bacteria extremely suitable for delivery of said antigen and possibly said immune-suppressing compound. *L. lactis* is a non-pathogenic, non-invasive, non-colonizing gram-positive bacterium. A variety of genetically modified *L. lactis* strains is generated for local synthesis and delivery of immunomodulatory proteins to the intestinal mucosa. Furthermore, a biological containment system is established which makes clinical application of genetically engineered L. lactis a feasible strategy.

In one preferred embodiment said micro-organism is a Lactococcus lactis thyA mutant. A specially preferred embodiment uses a Lactococcus lactis thyA mutant, wherein the gene encoding the antigen has been used to disrupt the thyA gene.

Nutraceuticals & Medical Foods

It will be appreciated that the compounds and compositions of the invention may be used as nutraceuticals, functional or medical food, or as additives in said nutraceuticals, functional or medical food. Another embodiment provides a food or beverage, preferably fit for human consumption, which is comprised of a nutraceutical and a flavoring agent, wherein the nutraceutical is comprised of an extract from an agricultural product.

Nutraceuticals, whether in the form of a liquid extract or dry composition, are edible and may be eaten directly by humans, but are preferably provided to humans in the form of additives or nutritional supplements e.g., in the form of tablets of the kind sold in health food stores, or as ingredients in edible solids, more preferably processed food products such as cereals, breads, tofu, cookies, ice cream, cakes, potato chips, pretzels, cheese, etc., and in drinkable liquids e.g., beverages such as milk, soda, sports drinks, and fruit juices. Thus, in one embodiment a method is provided for enhancing the nutritional value of a food or beverage by intermixing the food or beverage with a nutraceutical in an amount that is effective to enhance the nutritional value of the food or beverage.

Another embodiment provides a method for enhancing the nutritional value of a food or beverage which comprises intermixing a food or a beverage with a nutraceutical to produce a nutritionally-enhanced food or beverage, wherein the nutraceutical is intermixed in an amount effective to enhance the nutritional value of the food or beverage, wherein the nutraceutical is comprised of an extract from a crop comprising the antigens of the present invention, and wherein the nutritionally-enhanced food or beverage may further comprise a flavoring agent. Preferred flavoring agents include sweeteners such as sugar, corn syrup, fructose, dextrose, maltodextrose, cyclamates, saccharin, phenyl-alanine, xylitol, sorbitol, maltitol, and herbal sweeteners e.g., Stevia.

The nutraceuticals described herein are intended for human consumption and thus the processes for obtaining them are preferably conducted in accordance with Good Manufacturing Practices (GMP) and any applicable government regulations governing such processes. Especially preferred processes utilize only naturally derived solvents. The nutraceuticals described herein preferably contain relatively high levels of health-enhancing substances Nutraceuticals may be intermixed with one another to increase their health-enhancing effects.

In contrast to nutraceuticals, the so-called "medical foods" are not meant to be used by the general public and are not available in stores or supermarkets. Medical foods are not those foods included within a healthy diet to decrease the risk of disease, such as reduced-fat foods or low-sodium foods, nor are they weight loss products. A physician prescribes a medical food when a patient has special nutrient needs in order to manage a disease or health condition, and the patient is under the physician's ongoing care. The label must clearly state that the product is intended to be used to manage a specific medical disorder or condition. An example of a medical food is nutritionally diverse medical food designed to provide targeted nutritional support for patients with chronic inflammatory conditions. Active compounds of this product are for instance one or more of the compounds described herein. Functional foods may encompass those foods included within a healthy diet to decrease the risk of disease, such as reduced-fat foods or low-sodium foods, or weight loss products. Hence, the present invention contemplates a food or beverage comprising a nutraceutical according to the invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

In addition, all terms used in the description of compounds of the present invention have their meaning as is well known in the art.

Control mice received BM9. At day 10, mice were challenged with 10 μg eDQ8d in 10 μl saline in the auricle of the ear. DTH responses are expressed as the mean in increase 24 hours after injection, following subtraction of ear-thickness before eDQ8d challenge. Results summarize data of 3 independent experiments including 6 mice per group.

Figure 6:
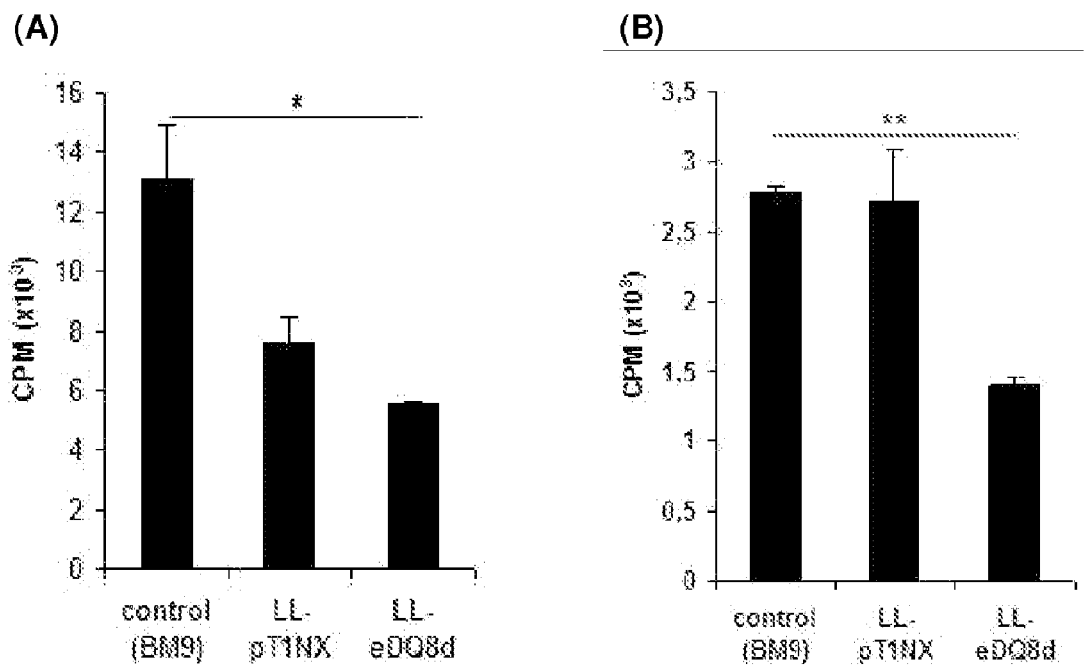

FIG. 6: After the DTH measurements, spleens (A) and inguinal lymph nodes (B) of the BM9 (control), LL-pT1NX and LL-eDQ8d groups were isolated and ex vivo restimulated with 50 μg eDQ8d peptide. eDQ8d-specific proliferative response of bulk splenocytes (p=0.048) and inguinal lymph node cells (p=0.0022) were expressed as the mean cpm.

Figure 7:
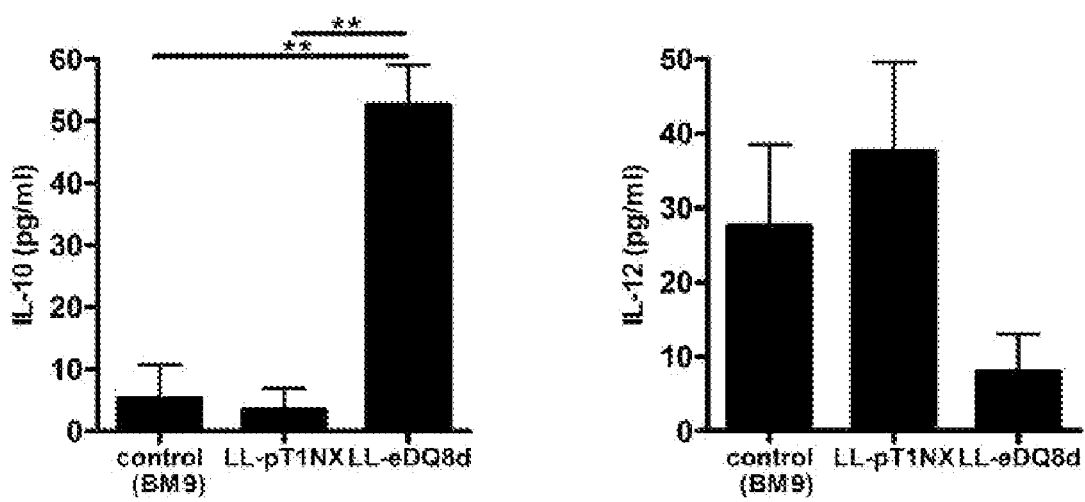
Figure 7:
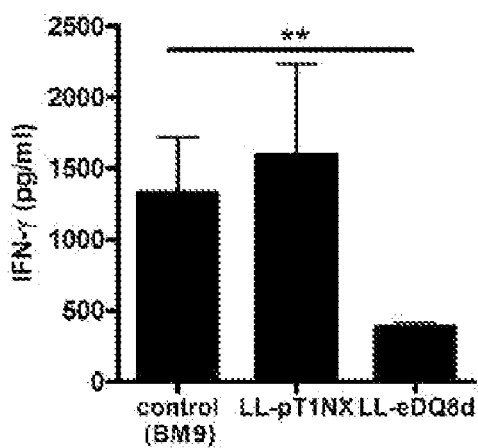

FIG. 7: Cytokine measurements in the supernatant of spleen (A) and inguinal lymph node cells (B) were performed 24 hours after restimulation. Results are means of cytokine secretion in pg/ml representative of at least two individual experiments.

Figure 8:
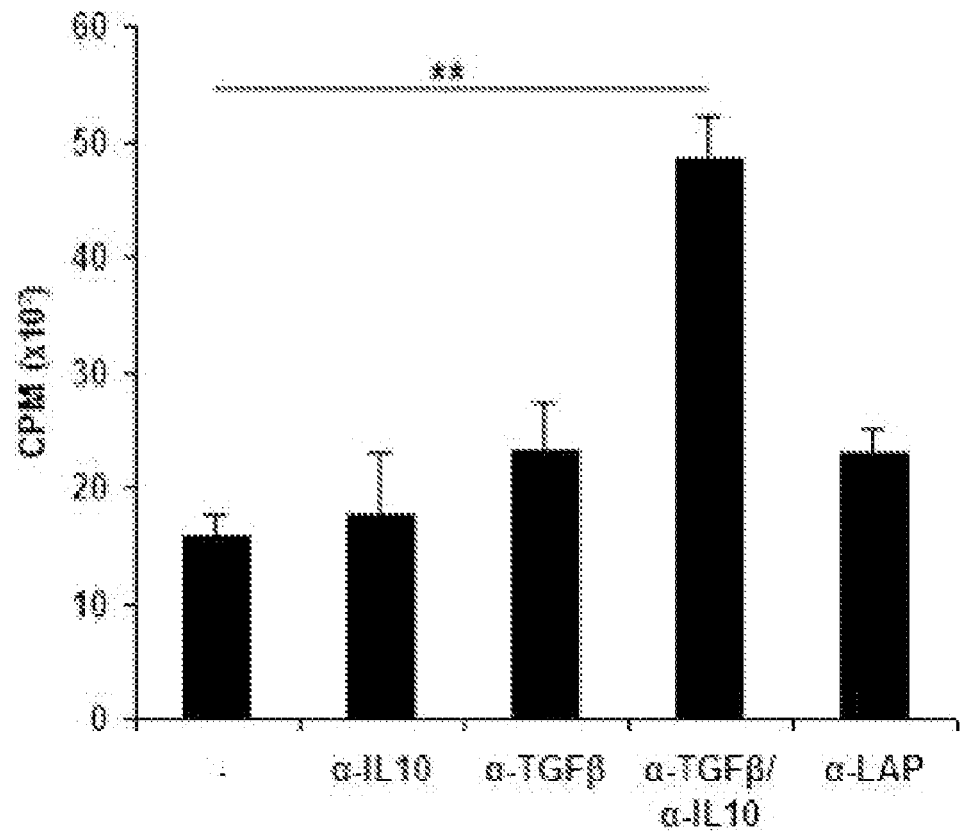

FIG. 8: Decreased splenic eDQ8d-specific proliferation depends on IL-10 and TGF-β

EXAMPLES

Example A

Induction of OVA-Specific Tolerance by Genetically Modified *Lactococcus lactis* Delivering OVA to OVA-Sensitized Wild Type Mice Introduction For this purpose we genetically engineered OVA secreting LL (LL-OVA) and evaluated the induction of systemic tolerance in a therapeutic model for autoimmunity/allergy, namely the OVA immunization model.

Materials and Methods

Bacteria and media: The *Lactococcus lactis* MG1363 (LL) strain was genetically modified and used throughout this study. Bacteria were cultured in GM17E medium consisting of M17broth (Difco Laboratories, Detroit, Mich.) supplemented with 0.5% glucose and 5 μg/ml erythromycin (Abbott). Stock suspensions of LL strains were stored at −20° C. in 50% glycerol in GM17E medium. Stock suspensions were diluted 500-fold in GM17E medium and incubated at 30° C. overnight. Within 16 h they reached a saturation density of $2 \times 10^9$ colony forming units (CFU) per ml. Bacteria were harvested by centrifugation and resuspended in BM9 medium at $2 \times 10^{10}$ bacteria/ml. Each mouse received 100 μl of this suspension daily through an intragastric catheter.

Plasmids: The mRNA sequence encoding *Gallus gallus* Ovalbumin was retrieved from Genbank (accession number AY223553) and from published data. Total RNA was isolated from chicken uterus and cDNA was synthesized using 2 μg total RNA, 2 μM oligo dT primers (Promega Corporation Benelux, Leiden, The Netherlands), 0.01 mM DTT (Sigma-Aldrich, Zwijndrecht, The Netherlands), 0.5 mM dNTP (Invitrogen, Merelbeke, Belgium), 20 U Rnasin (Promega Incorporation Benelux) and 100 U superscript II reverse transcriptase (Invitrogen) in a volume of 25 μl. An OVA cDNA fragment was amplified by Polymerase Chain Reaction (PCR) using the following primers: forward 5'-GGCTCCATCGGTGCAGCAAGCATGGAATT-3' (SEQ ID NO: 9) and reverse 5'-ACTAGTTAAGGGGAAACACATCTGCCAAAGAAGAGAA-3'(SEQ ID NO: 10). Reaction conditions were 94° C. for 2 min followed by 30 cycles at 94° C. for 45 seconds, 62° C. for 30 seconds and 72° C. for 90 seconds. The amplified fragment was fused to the Usp45 secretion signal of the erythromycin resistant pT1NX vector, downstream of the lactococcal P1 promotor17. MG1363 strains transformed with plasmids carrying OVA cDNA were designated *L. lactis* secreting OVA (LL-OVA). The *L. lactis*-pTREX1, which is MG1363 containing the empty vector pTREX1, served as control (LL-pTREX).

Mice: Seven-week old female Balb/c mice were obtained from Charles River Laboratories (Calco, Italy) and were housed in a conventional animal facility under specific pathogen-free conditions. The animal studies were approved by the Ethics Committee of the Department for Molecular Biomedical Research at Ghent University (file No. 07/029).

Antigen: Intact, LPS-free OVA grade V protein was used as antigen in all experiments (Sigma Aldrich).

Immunization of mice and induction of oral tolerance: Balb/c mice were immunized by s.c. injection of 100 μg OVA in 100 μl of a 1:1 mixture of CFA (Difco, BD Bioscience, Erembodegem, Belgium) and saline solution at the base of the tail on the first day. LL-OVA, LL-pTREX1 or 1 μg purified OVA dissolved in 100 μl BM9 were administered daily on days 7-11, 14-18, 21-25 and 28-31 (regime 1), and on days 21-25 and 28-31 (regime 2). Control mice received only BM9. Antigen or bacterial suspensions were introduced into the stomach using an 18-gauge stainless animal feeding needle. On day 21, a boost immunization was given by s.c. injection of 100 μg OVA in 100 μl of a 1:1 mixture of IFA (Sigma-Aldrich). Tolerance induction was assessed by DTH responses, measurement of cytokines and OVA-specific proliferation, and adoptive transfer experiments.

Delayed-type Hypersensitivity responses: Antigen-specific DTH responses were assessed by injection of OVA on day 31. Twenty-four hours later DTH measurements were performed. For measurement of antigen-specific DTH responses, mice were challenged with 10 μg OVA in 10 μl A saline in the auricle of the ear. Ear swelling, defined as the increase in ear thickness due to challenge, was measured in a blinded fashion 24 h after challenge using a digital micrometer (Conrad, Belgium). The DTH responses were expressed as the difference in ear thickness before and after the OVA challenge for both ears.

OVA-specific proliferation and cytokine assays: On day 39, the spleens were harvested and the splenocytes were assessed for OVA-specific proliferation and cytokine production. Single cell suspensions of spleens were prepared by passing the cells through 70-μm cell strainers (Becton/Dickinson Labware). Erythrocytes in the cell suspensions were lysed by incubation with red cell lysis buffer. CD4$^+$ T cells were enriched using CD4$^+$ T cell isolation kit and midiMACS columns (Miltenyi Biotec, Germany).

To assay proliferation of total splenocyte populations, $2 \times 10^5$ cells were cultured in 96-well U-bottom plates in a total volume of 200 μl complete medium [i.e., RPMI-1640 containing 10% fetal calf serum (FCS), 10 U/ml penicillin, 10 μg/ml streptomycin, 2 mM L-glutamax, 0.4 mM sodium pyruvate] either alone or with OVA, added at concentrations ranging from 1.2 to 100 μg/ml. The proliferation was further assessed by 5,6-CFSE labelling (Invitrogen, Merelbeke, Belgium). The splenocytes were resuspended in PBS at $10^7$/ml and incubated in a final concentration of 10 μM CFSE for 12 min at 37° C. Labelled cells were washed twice with ice-cold complete medium before being cultured at $2 \times 10^5$ cells in 96-well U-bottom plates in a total volume of 200 μl complete medium with 100 μg/ml OVA. After 90 h of culture at 37° C. and 5% $CO_2$ in a humidified incubator, the cells were harvested and the cells were stained with allophycocyanin-labeled anti-CD4 (BD, Biosciences) and proliferation was determined using flow cytometry (FACSCanto, BD Biosciences).

To assay proliferation of CD4+ T cells, 2×10^5 cells CD4+ T cells were cultured in 96-well U-bottom plates with mitomycin C treated-OVA loaded splenocytes, acting as antigen presenting cells, at ratios 1/1, 1/0.3, 1/0.1, 1/0.03 and 1/0 in a total volume of 200 µl complete medium. Cells were cultured for 90 h at 37° C. and 5% $CO_2$ in a humidified incubator. For proliferation assays, 1 µCi/well [3H]-thymidine was added for the last 18 h of culture, DNA was harvested on glass fibre filter mats (Perkin Elmer, Boston, USA), and DNA-bound radioactivity was measured on a scintillation counter (Perkin Elmer). For cytokine measurements, supernatants of the cell cultures used in the different proliferation assays were collected after 72 h of culture and frozen at −20° C. Cytokine production was quantified using the Mouse Flex Set Cytometric Bead Array (BD Biosciences, Mountain View, Calif., USA).

Adoptive transfer experiments: On day 39, the spleens were collected from the treatment groups. Single cell suspensions were obtained by mincing the spleens and straining them through 70-µm cell strainers (Becton/Dickinson Labware). The cell suspensions were enriched for CD4+ T cells, as described above. CD4+-enriched cells were adoptively transferred to naïve BALB/c acceptor mice by the i.v injection of 1×10^6 CD4+ T cells. One day after adoptive transfer, all mice were sensitized by injection 100 µg OVA/25 µl saline/ 25 µl IFA (Sigma-Aldrich) s.c. at the tail base, and 5 days thereafter, mice were challenged according to the DTH protocol described above.

Statistical analysis: Significance of differences between groups in ear-thicknesses and cytokine measurements were tested using one-way ANOVA. Statistical significance is indicated as * ($p<0.05$) or ** ($p<0.01$).

Results

Figure 1:
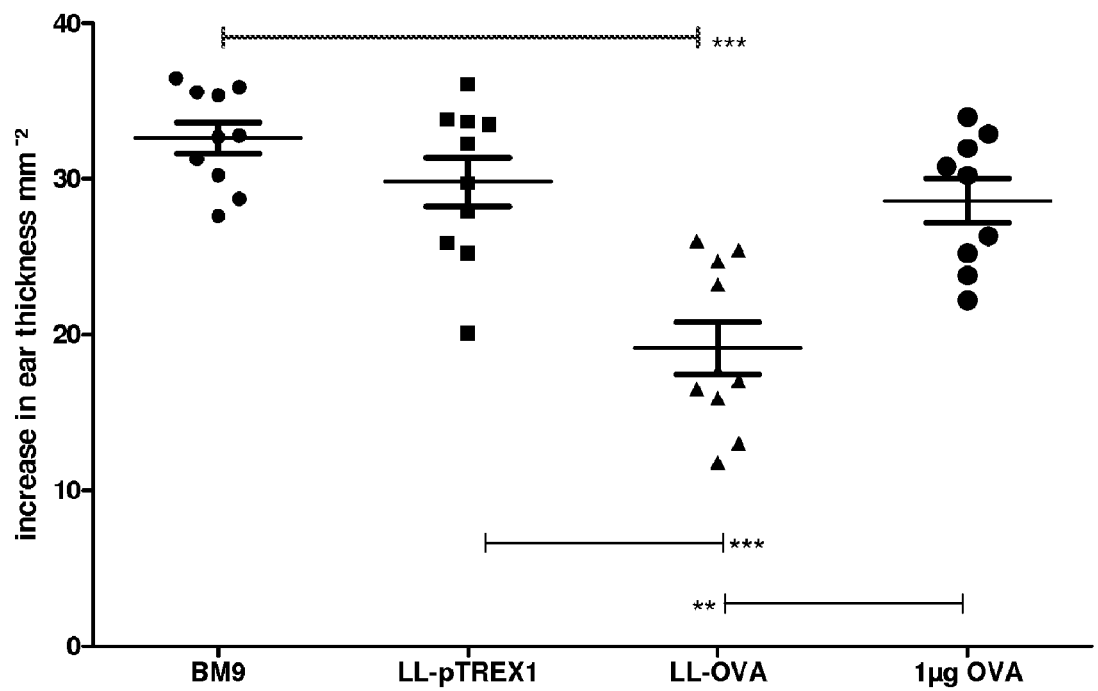
FIG. 1: Oral feeding of LL-OVA significantly reduces DTH responses. Balb/c mice were sensitized by s.c. injection of OVA/CFA on days 0 and received a boost immunization of OVA/IFA on day 21. Mice were orally treated with BM9, LLpTREX1, LL-OVA and 1 µg OVA on days 7-11, 14-18, 21-25 and 28-31. On day 31, mice were challenged with 10 µg Ova In 10 µl saline in the auricle of the ears. The DTH responses were expressed as the difference in ear thickness before and after the OVA challenge for both ears 24 h postchallenge.

LL-OVA Significantly Enhance the Tolerance-Inducing Capacity in OVA Immunization Model Compared to Free OVA To study the induction of oral tolerance, mice were orally fed as described above. Administration of LL-OVA to OVA-sensitized BALB/c mice led to a significant decrease in DTH response compared to the sensitized control mice (BM9 group) and mice treated with LL-pTREX1 or 1 µg purified OVA (FIG. 1)

Figure 2:
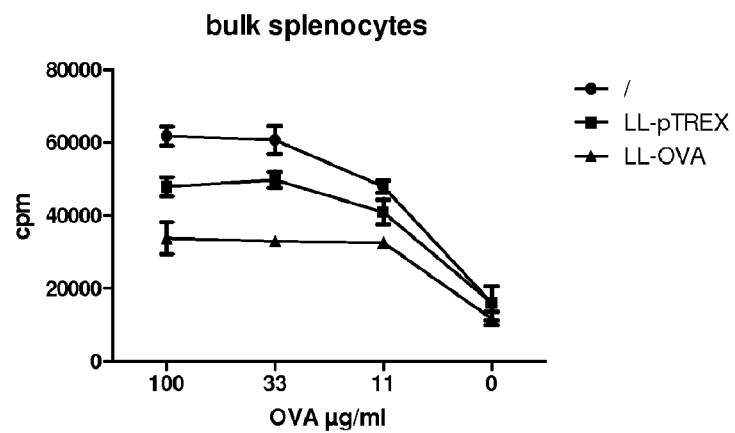
FIG. 2: Oral feeding of LL-OVA significantly reduces the OVA-specific proliferation (A) and IFN-γ (B), IL-6 (C) and IL-10 (D) production of bulk splenocytes. Balb/c mice were sensitized by s.c. injection of OVA/CFA on days 0 and received a boost immunization of OVA/IFA on day 21. Mice were orally treated with BM9, LLpTREX1 and LL-OVA on days 21-25 and 28-31. On day 31, bulk splenocytes were isolated and tested for OVA-specific proliferation, which is expressed as the mean cpm±SEM at different OVA concentrations, and for IFN-γ, IL-6 and IL-10 production after 72-hour ex vivo stimulation with 100 µg/ml OVA.
Figure 2:
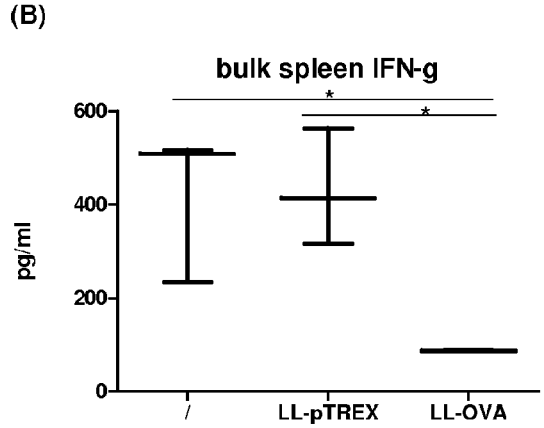
Figure 2:
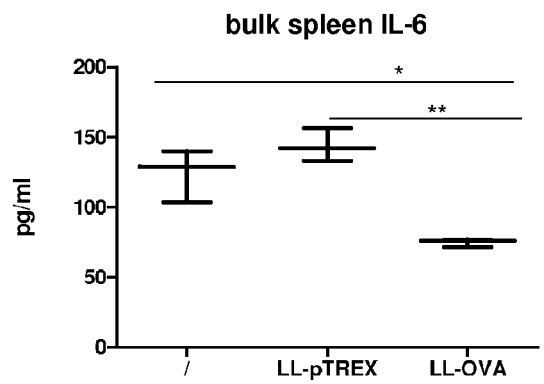
Figure 2:
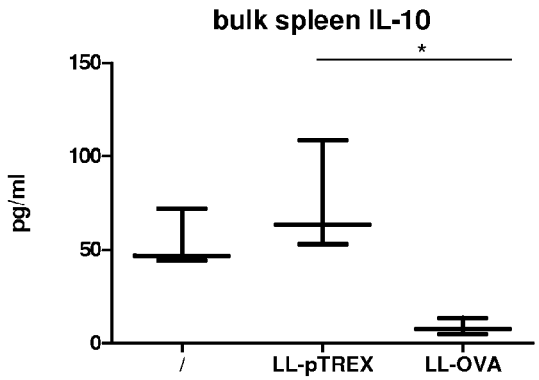

These data were accompanied by a significant decreased proliferative capacity and IFN-γ, IL-10 and IL-6 production (FIG. 2) of the bulk splenocytes of LL-OVA treated mice as compared to BM9 or LL-pTREX1-treated groups. LL-OVA Enhances Oral Tolerance Via CD4+ T Cells.

Figure 3:
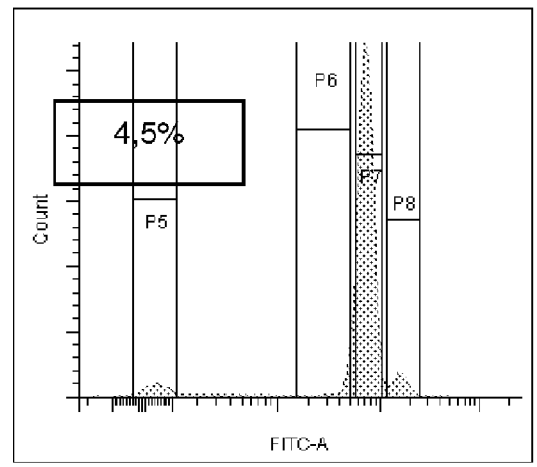
FIG. 3: Oral feeding of LL-OVA significantly reduces the OVA-specific proliferation of CD4$^+$ splenic T cells. Balb/c mice were sensitized by s.c. injection of OVA/CFA on days 0 and received a boost immunization of OVA/IFA on day 21. Mice were orally treated with BM9 (A), LLpTREX1 (B) and LL-OVA (C) on days 21-25 and 28-31. On day 31, bulk splenocytes were isolated and OVA-specific proliferation of CD4$^+$ splenic T cells by CFSE and CD4-APC labelling and flow cytometric analysis after 90 h ex vivo restimulation with 100 µg/ml OVA.
Figure 3:
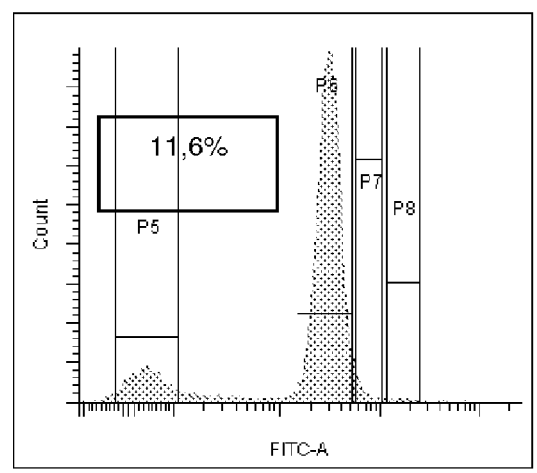
Figure 3:
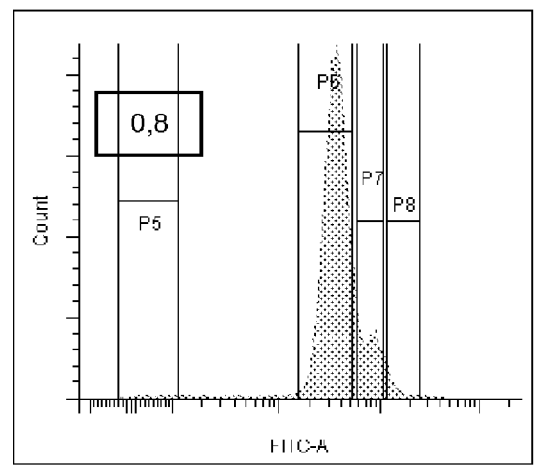
Figure 4:
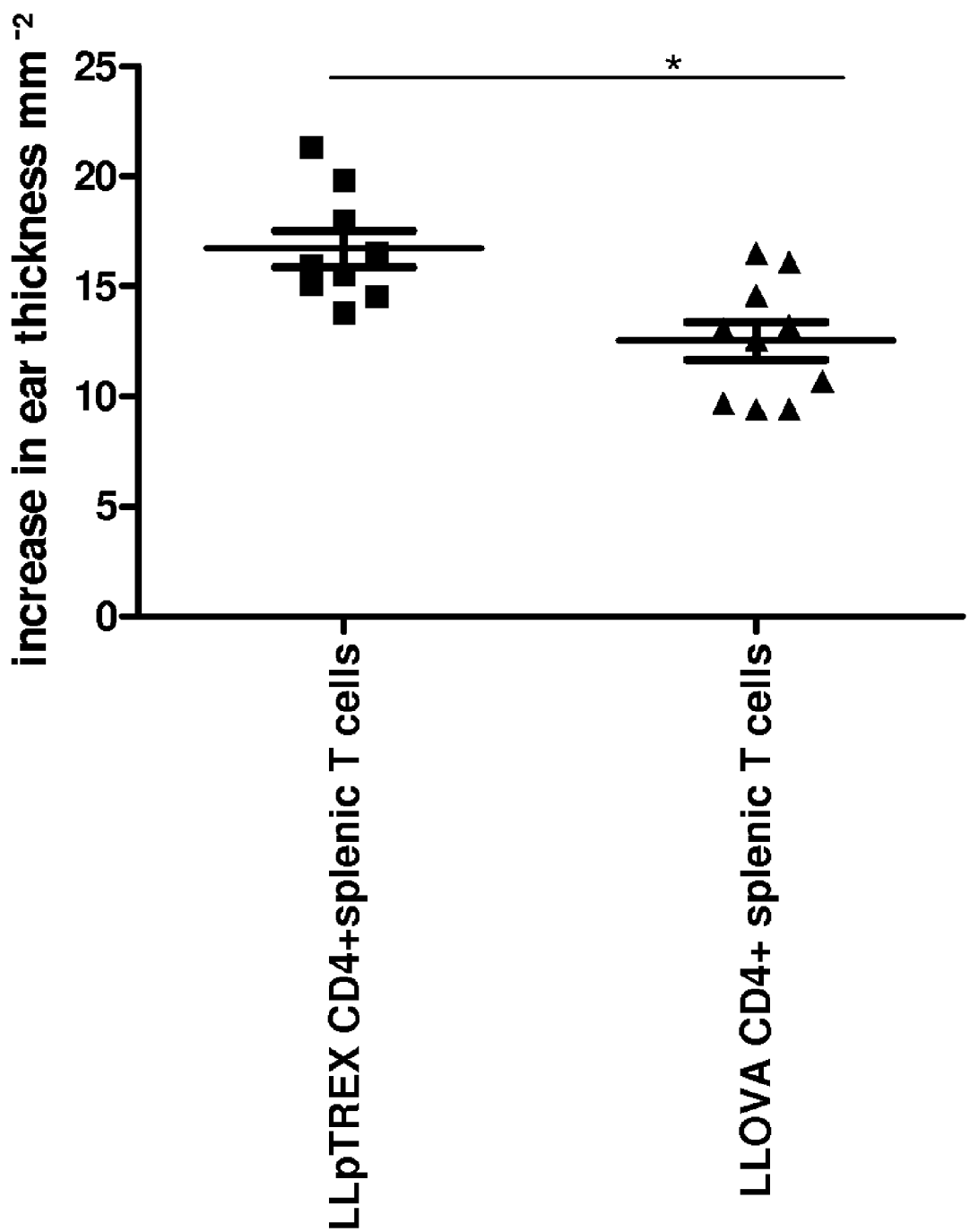
FIG. 4: CD4$^+$ T cells of LL-OVA treated mice transfer tolerance to naïve recipients. Balb/c mice were sensitized by s.c. injection of OVA/CFA on days 0 and received a boost immunization of OVA/IFA on day 21. Mice were orally treated with BM9, LLpTREX1 and LL-OVA on days 21-25 and 28-31. On day 31, CD4$^+$ splenic T cells were isolated and tested for tolerance transfer capacity. Transfer of tolerance by CD4$^+$ splenic T cells from LL-OVA and LL-pTREX treated mice to the naïve recipients was assessed by sensitizing and challenging the latter for a DTH response, that is expressed as the difference in ear thickness before and after the OVA challenge for both ears 24 h postchallenge.

To assess whether CD4 T cells mediate the induction of oral tolerance, the OVA-specific proliferative CD4 T cell response in the splenocytes was studied. Flow cytometry demonstrated that only 0.8% of the CD4+ splenic T cells proliferate after OVA restimulation in the LL-OVA group compared to 4.5% and 11.6% in the BM9 and LL-pTREX1 groups (FIG. 3). Furthermore, adoptive transfer CD4+ splenic T cells from the LL-OVA treated group to naïve BALB/c mice demonstrated that these cells could transfer tolerance, as these cells were able to reduce the DTH response after immunizing and challenging the acceptor mice with OVA (FIG. 4).

Conclusion

Here, we demonstrated that intragastric administration of OVA-secreting *L. lactis* suppresses OVA-specific T cell responses via the induction of CD4+ regulatory. We demonstrated that this immune tolerance induction is more potent than free OVA protein, and that this could be established in a therapeutic setting.

Example B

Induction of Antigen-Specific Oral Tolerance by Genetically Modified *Lactococcus lactis* Delivering DQ8-Specific Immunodominant Gliadin Epitopes to Gluten-Sensitized Class II Transgenic Mice Introduction Celiac disease, also known as celiac sprue or gluten-sensitive enteropathy, is a chronic inflammatory disease that develops from an immune response to specific dietary grains that contain gluten. Celiac is a complex multigenic disorder that is strongly associated with the genes that encode the human leukocyte antigen variants HLA-DQ2 or HLA-DQ8. One of the most important aspects in the pathogenesis of Celiac is the activation of a T-helper 1 immune response. This arises when antigen-presenting cells that express HLA-DQ2/ DQ8 molecules present the toxic gluten peptides to CD4(+) T-cells. Both classes of gluten proteins, gliadins and glutenins, contain peptides that bind DQ2 and DQ8. It is generally accepted that the immune response, such as the production of IFN-γ from gluten-specific T cells, triggers destruction of the mucosa in the small intestine of celiac disease patients. Hence, the activation of a detrimental immune T cell response in the intestine of celiac disease patients appears to be key in the initiation and progression of the disease.

Antigen-specific immune suppression is an attractive therapeutic goal for the treatment of celiac disease. Active delivery of recombinant gluten proteins/peptides at the intestinal mucosa by genetically modified *Lactococcus lactis* (LL) provides a novel therapeutic approach for the induction of tolerance. For this purpose we genetically engineered deamidated DQ8 epitope secreting LL (LL-eDQ8d) and evaluated the local and systemic immune response in gluten-sensitized NOD AB° DQ8 class II transgenic mice after oral supplementation.

Here, we demonstrate that oral delivery of gliadin peptide producing *L. lactis* suppresses gliadin-specific immune responses via the induction of antigen-specific CD4+ regulatory T cells.

Materials and Methods

Bacteria and media: The *Lactococcus lactis* MG1363 (LL) strain was genetically modified and used throughout this study. Bacteria were cultured in GM17E medium, being M17 broth (Difco Laboratories, Detroit, Mich.) supplemented with 0.5% glucose and 5 µg/ml erythromycin (Abbott). Stock suspensions of LL strains were stored at −20° C. in 50% glycerol in GM17E medium. Stock suspensions were diluted 200-fold in GM17E medium and incubated at 30° C. overnight. Within 16 h of culture, a saturation density of 2×10^9 colony forming units (CFU) per ml was reached. Bacteria were harvested by centrifugation and 10-fold concentrated in BM9 inoculation buffer at 2×10^9 bacteria/100 µl. For treatment, each mouse received 100 µl of this suspension daily by intragastric catheter.

Plasmids: The sequence encoding the deamidated DQ8 epitope, (encoding DQ8d: caa tac cca tca ggt gaa ggt tca ttc caa cca tca caa gaa aac cca caa gct (SEQ ID NO: 1)), was retrieved from published data. In summary, two glutamine residues within the alpha-gliadin peptide were changed into glutamic acids to stimulate the deamidated immunodominant alpha-gliadin response for the DQ8 carrying celiac disease patients, and this epitope is recognized by T cells of these mice. The DQ8d cDNA fragment was synthetically constructed (Operon, The Netherlands) and amplified by Polymerase Chain Reaction (PCR) using the following forward and reverse primers 5'-caatacccatcaggtgaaggttc-3' (SEQ ID NO: 11) and 5'-cgactagttaagcttgtgggttttcttgtgat-3' (SEQ ID NO: 12). For detection purposes an e-tag (e) was attached to the fragment, consisting of the following sequence ggt gct cca gtt cca tac cca gat cca ctt gaa cca cgt (SEQ ID NO: 13). To add the e-tag to the 5' end of DQ8d gene, the PCR product that was produced in step 1 (DQ8d) was used as template in a PCR with oligonucleotides 5'-ggtgctccagttccatacccagatc-cacttgaaccacgtcaatacccatca-3' (SEQ ID NO: 14) and 5'-cgac-tagttaagcttgtgggttttcttgtgat-3' (SEQ ID NO: 15). The amplified fragment was fused to the Usp45 secretion signal of the erythromycin resistant pT1 NX vector, downstream of the lactococcal P1 promotor. MG1363 strains transformed with plasmids carrying eDQ8d cDNA were designated *Lactococcus lactis* secreting eDQ8d (LL-eDQ8d). The LL-pT1 NX, which is MG1363 containing the empty vector, pT1 NX, served as control.

Functional analysis secreted epitopes: For functional analysis of the secreted eDQ8d epitope a proliferation assay with human T cell clones derived from the intestines of celiac disease (CD) patients was performed. Bacteria were grown overnight as described before, deluded 1:50 and grown for another 4 or 6 hours respectively. T cell clones specific for gluten were generated from a small intestinal biopsy taken from patient S, an adult Dutch CD patient that had been on a gluten-free diet for several years. The patient gave informed consent to the study, which was approved by the hospital ethics committee. The patient was typed serologically to be HLA-DR3/4, DQ2/8, thus carrying both CD-associated DQ dimers. T cell clone 1129 was found to respond to an alpha-gliadin derived peptide with a minimal 9 amino acid core QGSFQPSQQ, when bound to HLA-DQ8. Deamidation of the P1 and/or P9 glutamine residue (Q) into glutamic acid (E) by the activity of tissue transglutaminase was found to substantially enhance the T cell stimulatory capacity of this gluten peptide. Proliferation assays were performed in duplicate or triplicate in 150 µl culture medium (Iscoves) in 96-well flat-bottomed plates (Falcon) using $10^4$ T cells stimulated with $10^5$ HLA-DQ-matched and 3000 RAD irradiated Peripheral blood mononuclear cells in the absence or presence of supernatant at several concentrations. After 48 hours, cultures were pulsed with 0.5 uCi of [$^3$H]-thymidine, harvested 18 hours thereafter upon which $^3$H-thymidine incorporation was determined as a measure for proliferation.

Mice: Transgenic mice that express HLA-DQ8 in an endogenous MHC II-deficient background (AB° DQ8$^+$) were backcrossed to NOD mice for 10 generations and intercrossed to produce congenic NOD AB° DQ8$^+$ mice. Seven to sixteen week old mice were used for the experiments. Mice were weaned and maintained in a conventional animal facility until 8-12 weeks of age.

Antigen and Antibodies: Deamidated DQ8 epitopes with (GAPVPYPDPLEPRQYPSGEGSFQPSQENPQA (SEQ ID NO: 16)) and without (QYPSGEGSFQPSQENPQA (SEQ ID NO: 2)) e-tag were synthesized. For T-cell phenotyping, CD4 and CD25 antibodies were purchased from BD-Biosciences (San Jose, Calif.), and APC anti-Foxp3 staining kits were purchased from eBiosciences (San Diego, USA) respectively. Anti-IL-10 neutralising monoclonal antibody (1 µg/ml, clone JES052A5), TGF-β neutralizing monoclonal antibody (1 µg/ml, clone 1D11) and LAP neutralizing antibodies (1 µg/ml, clone 27235) were obtained from R&D systems (Minneapolis, Minn.).

Oral feeding and DTH (Delayed-type hypersensitivity) reaction: NOD AB° DQ8 mice on a gluten free chow were sensitized by subcutaneous injection of 100 µg deamidated eDQ8 peptides in 100 µl of a 1:1 CFA (purchased from Difco of Becton, Dickinson and Company, San Jose, Calif.) saline solution in the tail base at day 1. The peptide used for the sensitization had the same sequence as the secreted epitope. Mice were fed BM9 as a negative control, LL-pT1NX or LL-eDQ8d [all at days 1-10 dissolved in 100 µl BM9]. Feedings were performed by intragastric administrations of antigen or bacterial suspensions using an 18-gauge stainless gavage needle. Ten days after immunization, antigen-specific DTH responses were assessed. Twenty-four hours thereafter DTH measurements were performed. For measurement of antigen-specific DTH responses, mice were challenged with 10 µg eDQ8d in 10 µL1 saline in the auricle of the ear. The increase in ear thickness was measured in a blinded fashion using an engineer's micrometer (Mitutoyo, Tokyo, Japan) at 24 h after challenge. DTH responses were expressed as the difference in increase 24 hours after eDQ8d injection, following subtraction of ear-thickness before challenge. Subsequently mice were sacrificed, spleen and lymph nodes were harvested and cells were assessed for DQ8d-specific proliferation and cytokine production. For e-tag interference NOD AB° DQ8 mice were immunized with 100 µg deamidated DQ8 peptides with (eDQ8d) or without E-tag (DQ8d) in 100 µl of a 1:1 Complete Freund's Adjuvant (CFA, Difco, BD) saline solution in the tail base at day 1. At day 7 mouse DTH measurements were performed as described above with 10 µg DQ8d with or without e-tag, corresponding to the peptide used for the immunization.

Cell cultures, proliferation and cytokine production assays: Cell suspensions of spleen and lymph nodes were prepared at day 11 of the experiment by homogenizing the tissue with a tissue grinder in 1×PBS. Erythrocytes were removed from the spleen cell suspensions by incubation with ACK (Ammonium Chloride/Potassium (lysing buffer)). Cells were incubated in 96-well microtiter plates at $5 \times 10^5$ cells/well in 0.2-ml volumes at 37° C. in RPMI 1640 (1.5% Hepes, 1% Penstrep and 10% FBS) with supplements containing either medium alone, 10 µg Con A, or 50 µg eDQ8d epitope. In a separate experiment IL-10, TGF-β, IL10&TGF-β or LAP neutralizing antibodies were added to splenocytes of LL-eDQ8d treated mice. After 24 h, proliferation was assessed by addition of 1 µCi/well [$^3$H]-thymidine for the last 24 h of culture. DNA-bound radioactivity was harvested onto glass fiber filter mats and thymidine-incorporation measured on a scintillation counter (Perkin Elmer). Results were expressed as mean cpm of triplicate wells. For cytokine measurements, supernatants of the cell cultures used in the different proliferation assays, described above, were collected after 24 h of culture and frozen at −20° C. until cytokine analysis was performed. Cytokine production was quantified using the Mouse Inflammation Cytometric Bead Assay (BD Biosciences).

Flow cytometric analysis: Spleens and gut-associated lymph node tissue (GALT) of BM9, LL-pT1 NX or LL-eDQ8d treated mice were isolated, prepared as described above and stained for CD4, CD25 and Foxp3. Intracellular staining was performed for Foxp3 according to the manufacturer's instructions (eBiosciences, San Diego, Calif.) and subsequently measured using flow cytometry on a Becton Dickinson FACSCaliburs. For analysis cells were gated on CD4$^+$CD25$^+$ and CD4$^+$CD25$^-$ subpopulations and within these populations Foxp3 histograms were used to determine Mean Fluorescence Intensity (MFI).

Statistical analysis: Results from cytokine measurements are expressed as means±SEM. eDQ8d-specific proliferation, ear-thickness- and cytokine measurements were tested for significance using one-way ANOVA followed by the student's t-test comparison: two samples assuming equal variance, to determine the differences between individual groups. For all tests a p value <0.05: *, <0.01: ** was used to indicate statistical significance for both tests.

Results

Mucosal Delivery of eDQ8d Epitopes by *L. lactis* Significantly Decreases the DQ8d-Induced DTH Response and Proliferative Capacity of Bulk Spleen and Inguinal Lymph Node Cells.

Figure 5:
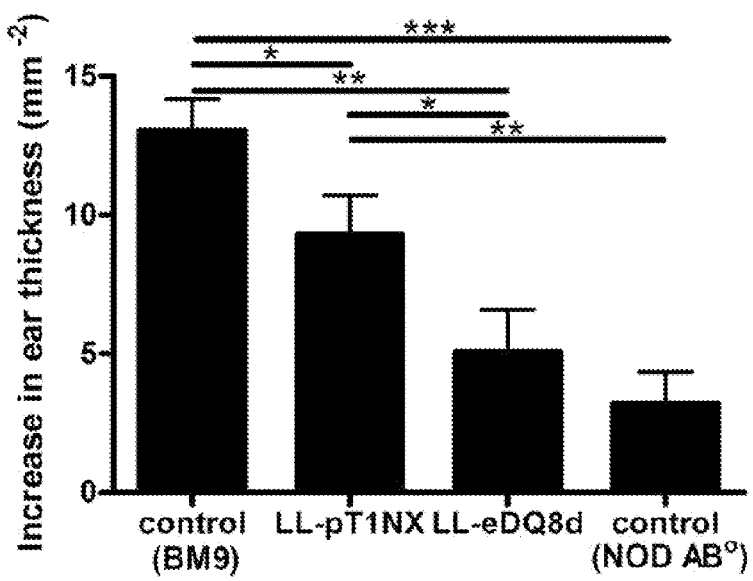
FIG. 5: NOD AB° DQ8 transgenic mice were immunized by s.c. injection of 100 µg eDQ8d in CFA at day 1. Mice were orally treated with LL-eDQ8d or LL-pT1NX at days 1-10.

Daily intragastric administration of LL-eDQ8d in eDQ8d-immunized NOD AB° DQ8 class II transgenic mice led to a significant decrease in DTH response compared to the sensitized negative control mice (FIG. 5). Control mice (fed BM9) were clearly immunized to eDQ8d, but daily intra-gastric administration of LL-eDQ8d significantly reduced the DTH ($13.1 \times 10^{-2}$ mm vs $5.1 \times 10^{-2}$ mm, p=0.0031). Ear swelling was also slightly reduced in LL-pT1NX-treated mice compared to controls ($9.3 \times 10^{-2}$ mm vs $13.1 \times 10^{-2}$ mm p=0.0343) but to a much lesser degree than in LL-eDQ8d treated mice. Non DQ8 transgenic NOD AB° mice showed only a minor increase in ear thickness ($3.2 \times 10^{-2}$ mm). These data indicate that orally administered LL-eDQ8d suppress systemic inflammatory T-cell responses in immunized NOD AB° DQ8 transgenic mice and that the secreted antigen is necessary for induction of a significant tolerogenic effect. These data were accompanied by a significant decreased proliferative capacity of the splenocytes and inguinal lymph node cells (FIG. 6). The reduced proliferative response was accompanied by a significant up-regulation of IL-10 and a downregulation of IL-12 production following ex vivo eDQ8d stimulation of splenocytes (FIG. 7). Moreover LL-eDQ8d significantly reduced the eDQ8d-induced IFN-γ production in the inguinal lymph nodes compared to the BM9 and LL-pT1NX treated mice. Together, these data indicate that LL-eDQ8d treatment suppresses T cell activation following eDQ8d stimulation and suggest that DC activation my also be modulated.

Decreased Splenic eDQ8d-Specific Proliferation Depends on IL-10 and TGF-β, and LL-DQ8d Treatment Significantly Increases Splenic and GALT Foxp3 Expression The functional importance of TGF-β, IL-10, and LAP (membrane-associated TGF-β) on the eDQ8d-specific splenic proliferative response was analyzed using neutralizing antibodies. IL-10-, TGF-β- or LAP-neutralizing antibodies did not significantly interfere with the decreased splenic proliferative response of LL-eDQ8d treated mice, but adding a combination of TGF-β and IL-10 neutralizing monoclonal antibodies completely abolished the decreased eDQ8d-specific proliferative capacity of splenocytes of LL-eDQ8d treated mice (FIG. 8). These data strongly suggest that LL-eDQ8d treatment is able to suppress T cell activation in eDQ8d-immunized NOD AB° DQ8 class II transgenic mice and that this suppression is dependent on both IL-10 and TGF-β. Moreover, a significant upregulation of Foxp3 was seen within the splenic CD4+CD25+as well as the CD4+CD25− cell population of the LL-eDQ8d treated mice compared to the control (BM9) (MFI 171 vs 61 and 35 vs 6, respectively). Remarkably, Foxp3 was also upregulated in the CD4+CD25− population in the gut-associated lymph node tissue (GALT) of the LL-eDQ8d treated mice compared to the BM9 treated (MFI 73 vs 30), but not in the GALT CD4+CD25+ population. LL-pT1NX feeding also induced some Foxp3 upregulation, but exclusively in the splenic CD4+CD25− T-cell population and to a lesser extent than LL-eDQ8d (MFI 15 vs 35, respectively).

Conclusion

Our data demonstrated that mucosal delivery of a gliadin derived peptide immunodominant for DQ8 mediated T-cell responses-by genetically modified *L. lactis*, induces suppression of local and systemic DQ8 restricted T-cell responses in NOD AB° DQ8 class II transgenic mice. Treatment resulted in an antigen-specific decrease of the proliferative capacity of the splenocytes and inguinal lymph node cells, which was critically dependent on the production of IL-10 and TGF-β and associated with a significant induction of Foxp3+ regulatory T-cells. Because this approach of antigen-delivering bacteria has the capacity for potentiating oral tolerance even in the setting of established hypersensitivity, it may be applicable for the treatment of celiac disease and possibly other autoimmune and/or allergic diseases.

Native DQ8 Epitope

The above experiments are repeated with the native α-gliadin epitope, i.e., QYPSGQGSFQPSQQNPQA (SEQ ID NO: 4), corresponding to residues 203-220 of the sequence retrievable via UniProtKB/TrEMBL entry Q9M4L6. Said native DQ8 epitope is encoded by the nucleotide sequence 5'-caa tac cca tca ggt caa ggt tca ttc caa cca tca caa caa aac cca caa get-3' (SEQ ID NO: 3).

The results with the native α-gliadin DQ8 epitope are essentially identical to the results described above for the deamidated α-gliadin DQ8 epitope.

Trial in Celiac Patients Using DQ8 Epitope

In a preliminary study, engineered *L. lactis* according to the invention are used as a therapeutic in a trial in patients with Celiac disease. Our findings provide promise that this approach is effective in an antigen-specific manner.

Celiac disease is an especially attractive target for this approach, due tot the ability of the LL to deliver the antigen at the site of the primary response to achieve both direct and bystander tolerance.

Trial in Celiac Patients Using DQ2 Epitope

No transgenic mice exist expressing HLA-DQ2 in an endogenous MHC II-deficient background, comparable to HLA-DQ8 mice as used above. Accordingly, the experiments described above for DQ8 epitopes were not possible in an appropriate mouse model. We therefore conduct some preliminary experiments in patients with celiac disease, using both native as well as deamidated α-gliadin DQ2 epitope.

Specifically, the above experiments are repeated using: deamidated DQ2 epitope LQLQPFPQPELPYPQPQLPYPQPELPYPQPQPF (SEQ ID NO: 6), encoded by the nucleotide sequence 5'-tta caa tta caa cca ttc cca caa cca gaa tta cca tac cca tta cca tac cca caa cca gaa tta cca tac cca caa cca caa cca ttc (SEQ ID NO: 5) and the native DQ2 epitope: LQLQPFPQPQLPYPQPQLPYPQPQLPYPQPQPF (SEQ ID NO: 8), encoded by the nucleotide sequence 5'-tta caa tta caa cca ttc cca caa cca caa tta cca tac cca tta cca tac cca caa cca caa tta cca tac cca caa cca caa cca ttc (SEQ ID NO: 7)

The results with the native and deamidated α-gliadin DQ2 epitope are essentially identical to the results described above for the α-gliadin DQ8 epitopes.

Example C

Induction of Tolerance to Clotting Factor VIII and Factor IX Following Oral Administration of *L. lactis* Secreting Said Factors Introduction Several therapeutic (recombinant) proteins, such as interferon's, factor VIII/IX and antibodies (Remicade) are administered at high doses over prolonged treatment periods. However, a complication associated with their use is the development of protein-specific immune responses, such as antibodies. These antibodies (Abs), also called inhibitors, render the therapeutic proteins less effective. Examples include the formation of inhibitors for factor VIII/IX in hemophilia, erythropoietin (Epo) in patients undergoing therapy for chronic renal failure, and IFN- in patients undergoing treatment for multiple sclerosis. Here, we demonstrate that oral delivery of the Factor VIII (and Factor IX) by *L. lactis* suppresses inhibitor formation to said factor via the induction of antigen-specific $CD4^+$ regulatory T cells.

Material and Methods

Bacteria and plasmids: The *L. lactis* strain MG1363 is used throughout this study. Bacteria are cultured in GM17 medium, i.e., M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and are incubated at 30° C. They reach a saturation density of $2\times10^9$ colony-forming units (CFU) per ml within 16 hours. Throughout this study, mixed bacterial suspensions are used. Therefore, the bacteria that are mixed are harvested by centrifugation and pellets of both bacterial cultures are concentrated 10-fold in BM9 medium (Schotte, Steidler et al., 2000). For treatment, each mouse receives 100 µl of this suspension by intragastric catheter.

Human FVIII and FIX cDNA or cDNA-fragments, representing FVIII- and FIX-specific $CD4^+$ T-cell epitopes, are amplified fused to the Usp45 secretion signal of the erythromycin resistant pT1 NX vector, downstream of the lactococcal P1 promotor.

MG1363 strains transformed with plasmids carrying human FVIII (and/or epitope fragment), FIX (and/or epitope fragment), were designated *L. lactis* secreting LL-FVIII, LL-FIX. LL-pT1 NX, which is MG1363 containing the empty vector pT1 NX, serve as control.

Quantification of FVIII and FIX: FVIII or FIX from LL-FVIII and LL-IX, respectively are determined using human FVIII and FIX-specific enzyme-linked immunosorbent assay (ELISA), that have been described previously (Chuah et al., 2003). The recombinant proteins are also analyzed by Western blot analysis and COATests and aPTT assays, as described (Chuah et al., 2003; VandenDriessche et al., 1999). The NH2-terminus of this protein is determined by automated Edman degradation. Since FVIII and FIX are normally expressed in the liver where they undergo extensive post-translational modifications, the clotting factors produced from the engineered *L. lactis* may be biologically inactive. However, these post-translational differences will likely have no repercussions on the ability of these *L. lactis*-produced recombinant proteins to induce immune tolerance. Indeed, most inhibitors that have been characterized in detail to date typically recognize amino acid residues (Villard et al., 2003), rather than glycosylated moieties.

Animals: Hemophilia A or B mice obtained by knocking-out the murine FVIII or FIX genes using homologous recombination in ES cells as described by (Bi et al., 1995) and Wang et al., (1997), are bred in the laboratory. These recipient mice generate neutralizing antibodies when challenged with purified recombinant FVIII or FIX antigen in the presence of CFA (Mingozzi et al., 2003). The inhibitor status can be monitored over time using Bethesda assays or anti-FVIII/anti-FIX specific ELISAs. Recipient mice challenged with FVIII or FIX (+CFA) typically develop inhibitors 2-3 weeks after antigenic challenge.

Experimental setting: 4-6 week-old mice receive FVIII, FIX, LL-FVIII, LL-FIX, or LL-pT1NX or LL-OVA (an irrelevant antigen) (1 or 10 µg). As a positive control for tolerance induction, we inject mice with adeno-associated viral vectors (AAV) expressing FIX from a hepatocyte-specific promoter. Recipient animals develop FIX-specific immune tolerance that prevents induction of anti-FIX antibodies upon subsequent challenge with FIX+CFA.

In a prophylactic setting, FVIII, FIX, LL-FVIII, LL-FIX alone are administered orally to hemophilia A or B mice using a gastric catheter, using different treatment intervals and doses. These recipient mice are subsequently challenged with purified recombinant FVIII or FIX antigen, in the presence of CFA (Mingozzi et al., 2003). Control animals are exposed to LL-pT1NX and LL-OVA. Plasma is harvested by retro-orbital bleeding. The development of antibodies directed against FVIII or FIX is assessed using Bethesda assays (Kasper et al., 1975) or using a modified anti-FVIII or anti-FIX specific ELISA (VandenDriessche et al., 1999) at different time intervals.

In a therapeutic setting, hemophilia A or B mice are first immunized with FVIII or FIX, as described (Mingozzi et al., 2003). The inhibitor status is monitored over time using Bethesda assays or anti-FVIII/anti-FIX specific ELISAs. Mice with low or high inhibitor titers are subsequently treated with FVIII, FIX, LL-FVIII, LL-FIX alone using different treatment intervals and doses and inhibitor titers are determined over time. The specificity of the possible immune tolerance is assessed by challenging the mice that receive FVIII, FIX, LL-FVIII, LL-FIX alone with an irrelevant antigen (tetanus toxoid or Ova).

Cell cultures, proliferation and cytokine assay: Single cell suspensions of spleen and lymph nodes are prepared by passing the cells through 70 µm filter cell strainers (Becton/Dickinson Labware). Erythrocytes are removed from the spleen cell suspensions by incubation with red cell lysis buffer.

Proliferation assays of total splenocyte populations, $2\times10^5$ cells are cultured in 96-well U-bottom plates in a total volume of 200 µl complete medium either alone or with purified FVIII or FIX, and either with or without anti-IL-10 or anti-TGF-β neutralising monoclonal antibodies. FVIII and FIX is added at concentrations ranging from 1 to 100 µg/ml. The neutralizing antibodies are added at 1, 0.1 and 0.01 µg/ml. For proliferation assays of $CD4^+$ T cells and $CD4^+CD25^-$ T cell populations, $0.2\times10^5$ cells $CD4^+$ T cells or $CD4^+CD25^-$ T cells are cultured in 96-well U-bottom plates with $1\times10^5$ irradiated $CD4^-$cells, acting as antigen presenting cells, and FVIII or FIX (0 or 100 µg/ml) in a total volume of 200 µl A complete medium either with or without neutralizing antibodies. After 72 hr at 37° C. in a 5% $CO_2$ humidified incubator, proliferation is assessed by addition of 1 µCi/well $[^3H]$-thymidin. DNA-bound radioactivity is harvested 16-18 hr later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays are collected after 24, 48 and 72 h of culture and frozen at −20° C. until cytokine analysis is performed. Cytokine production is quantified using the Mouse Inflammation Cytometric Bead Assay (BD Biosciences, Mountain View, Calif., USA).

In vivo T regulatory activity assay: In order to test for active suppression of antibody formation in mice, splenocytes, bead-purified CD4+ T cells, CD4+CD25− or CD4+CD25+ T cells isolated from the different experimental *L. Lactis*-treated groups are adoptively transferred to naïve C3H/HeJ mice. Untreated mice are used as control. The number of transferred cells is $10^7$ for whole spleen cells, subpopulation-depleted spleen cells, or positively selected CD4+ cells and CD4+CD25− and CD4+CD25+ T cells. Recipient mice (n=4-5 per experimental cohort) were subcutaneously injected with 5 µg hF.IX in cFA 36 hours after adoptive transfer. Anti-hF.IX IgG titers in plasma were measured 2.5 weeks after immunization.

Results

LL-FVIII and LL-IX Significantly Enhances the Tolerance-Inducing Capacity of in Hemophilia A or B Mice Compared to Free FVIII or FIX To study the induction of oral tolerance, mice are orally fed as described above (experimental setting). Addition of LL-FVIII or LL-FIX significantly enhances the tolerance induction towards FVIII and FIX as the factor-specific proliferative response of splenocytes is significantly reduced in this group in comparison to the control and free FVIII and FIX groups. LL-FIIIV and LL-FIX Potentiate Oral Tolerance in Association with Reduced FVIII- and FIX-Specific Titers and IFN-γ and More IL-10 and TGF-β Production in Response to Said Factor.

To study the induction of oral tolerance, mice are orally fed as described above (experimental setting). FVIII and FIX-specific antibodies and cytokine production in response to said factor in splenocytes and lymph nodes are quantified as described above. The inhibitor formation and production of the proinflammatory cytokine, IFN-γ is strongly reduced and the immunosuppressive cytokines IL-10 and TGF-β is significantly increased in the LL-FVIII/FIX group in comparison to the control and free FVIII/IX groups. LL-FVIII/FIX Enhances Oral Tolerance Via CD4+ T Cells To assess whether CD4+ T cells mediate the induction of oral tolerance, the factor-specific proliferative CD4+ T-cell response is studied in the splenocytes and lymph nodes. Therefore, mice are orally fed as described above (experimental setting) and the factor-specific CD4+ T cell proliferation is determined as described in Cell cultures, proliferation and cytokine assay. The factor-specific CD4 T-cell response in the LL-FVIII/FIX group is significantly reduced in comparison to the control and free FVIII/IX groups.

Antigen-Induced T Regulatory Cells Following LL-FVIII/FIX Therapy Can Transfer Protection from Inhibitor Formation In Vivo In order to test for active suppression of antibody formation in mice treated with the oral tolerance protocol, we adoptively transfer splenocytes from the different treated groups as described above (In vivo T regulatory activity assay). Compared with controls and free FVIII/IX groups, antifactor IgG formation is significantly reduced in the LL-FVIII/FIX group, indicating activation of regulatory CD4+ T cells in our combination oral tolerance protocol.

Conclusion

Our data demonstrate that mucosal delivery of recombinant FVIII- or FIX secreting *L. lactis* are more potent than free FVIII or FIX in suppressing the formation of FVIII- and FIX-specific inhibitors in Hemophilia A and B mice respectively.

Example D

Induction of Tolerance to an Allergen, Der p 1 Following Oral Administration of *L. lactis* Secreting Said Allergen Introduction Allergic asthma is a chronic inflammatory disorder of the airways. It is characterized by reversible airway obstruction, elevated serum levels of allergen-specific immunoglobulin E, mucus hypersecretion and airway hyperresponsiveness (AHR) to ronchospasmogenic stimuli. Its symptoms are made worse by exposure to an allergen (e.g., tree, grass and weed pollen, dust and dust mites, mold, animal dander) to which the patient has been sensitized. Type 2 T-helper (Th2) lymphocytes play a crucial role in the initiation, progression and persistence of the disease. Current data suggest that Th2 responses to allergens are normally suppressed by regulatory T cells. Furthermore, suppression by this subset is decreased in allergic individuals. Here, we demonstrate that oral delivery of allergen by *L. lactis* suppresses asthma-like responses via the induction of antigen-specific CD4+ regulatory T cells.

Material and Methods

Two Mouse models of allergic asthma that mimics human disease are the Ova allergen model and the humanized SCID model.

The Ova allergen model: OVA-sensitized mice are inhalationally challenged with OVA aerosol that leads to Th2 cytokine-dependent eosinophilic airway inflammation, bronchial hyperreactivity, and IgE production, findings highly characteristic of human allergic asthma (Brusselle, 1994, Clin Exp Allergy 24:73; Kips et al., 1996, Am J Respir Crit. Care Med 153:535; Brusselle et al., 1995, Am J Respir Cell Mol Biol 12:254).

Bacteria: The *L. lactis* strain MG1363 is used throughout this study. Bacteria are cultured in GM17 medium, i.e., M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 500-fold in fresh GM17 and incubated at 30° C. They reached a saturation density of $2\times10^9$ colony-forming units (CFU) per mL within 16 hours. Bacteria are harvested by centrifugation and concentrated 10-fold in BM9 medium. For treatment, each mouse receives 100 µL of this suspension daily by intragastric catheter.

Plasmids: The mRNA sequence encoding *Gallus gallus* Ovalbumin is retrieved from Genbank (accession number AY223553). Total RNA is isolated from chicken uterus and cDNA is synthesized using 2 µg total RNA, 2 µM oligo dT primers (Promega Corporation Benelux, Leiden, The Netherlands), 0.01 mM DTT (Sigma-Aldrich, Zwijndrecht, The Netherlands), 0.5 mM dNTP (Invitrogen, Merelbeke, Belgium), 20 U Rnasin (Promega Incorporation Benelux) and 100 U superscript II reverse transcriptase (Invitrogen) in a volume of 25 µl. OVA cDNA fragment is amplified by Polymerase Chain Reaction (PCR) using the following conditions: 94° C. for 2 min followed by 30 cycles at 94° C. for 45 seconds, 62° C. for 30 seconds and 72° C. for 90 seconds, with the following forward and reverse primers 5'-GGCTC-CATCGGTGCAGCAAGCATGGAATT-3' (SEQ ID NO: 17) and 5'-ACTAGTTAAGGGGAAAC-ACATCTGCCAAA-GAAGAGAA-3' (SEQ ID NO: 18).

The amplified fragment is fused to the Usp45 secretion signal of the erythromycin resistant pT1 NX vector, downstream of the lactococcal P1 promotor.

MG1363 strains transformed with plasmids carrying OVA cDNA are designated LL-OVA. LL-pTREX1, which is MG1363 containing the empty vector, serve as control.

Quantification of OVA: OVA from LL-OVA are determined using an in house developed OVA-specific enzyme-linked immunosorbent assay (ELISA). Production of the recombinant proteins is also assessed by Western blot analysis.

Mice: BALB/c mice (6 to 8 weeks of age) are purchased from Charles River Laboratories (Calco, Italy). The mice are maintained under specific pathogen-free conditions.

Immunization of mice: Mice are immunized i.p. with 10 µg of OVA (grade V; Sigma-Aldrich) in 1 mg of aluminum hydroxide (alum). This immunization is repeated after 21 days (on days 0 and 21). Control mice receive a saline injection instead of the OVA/alum solution. 26 days after the immunization, sensitized mice inhale an aerosolized solution of 1% OVA dissolved in PBS for 10 min. OVA inhalation is conducted for 3 days in a row (days 47, 48, and 49). Control mice inhale PBS alone under the same conditions as used for the experimental group.

Induction of oral tolerance: Mice receive LL-OVA, LL-pTREX1, 1 µg OVA or BM9 on days 0-4,7-11, 14-18 and 21-25. As positive control for oral tolerance induction mice are fed 30 mg OVA by intragastric catheter that reduce bronchial eosinophilia and airway hyperresponsiveness, with high dose feeding being more effective than low-dose feeding.

Measurement of airway hyperresponsiveness (AHR): 24 h after the final inhalation (day 50), airway hyperresponsiveness is assessed by methacholine-induced airflow obstruction. The mice are exposed for 2.5 min to nebulized physiologic saline (Otsuka Pharmaceutical), followed by incremental doses (1-30 mg/ml) of nebulized methacholine. These mice are placed in a whole-body plethysmograph for 2.5 min following nebulization, and enhanced pause (Penh) is measured using Biosystem XA WBP system (Buxco Electronics). "Penh" represents pulmonary airflow obstruction and is calculated using the formula: $Penh=((Te-Tr)/(Tr-PEF/PIF))$, where Penh=enhanced pause (dimensionless), Te=expiratory time (seconds), Tr=relaxation time (seconds), PEF=peak expiratory flow (milliliters per second), and PIF=peak inspiratory flow (milliliters per second). Penh is measured and averaged approximately every 5 s, and the cumulative values are averaged as the Penh value for each time point. Airway hyperresponsiveness is expressed as PC200Mch (200% provocative concentration of methacholine), which is the concentration of methacholine that doubled the baseline Penh value.

Analysis of bronchoalveolar lavage fluid (BALF): After the measurement of airway hyperresponsiveness, bronchoalveolar lavage samples are obtained. The mice are euthanised by i.p. injection of overdose ketamin and xylazin, and then the lungs are lavaged with 0.5 ml of saline four times. The lavage fluid is centrifuged and the cells are resuspended in 1 ml of saline with 1% BSA. Total cell numbers are counted using a hemocytometer. Cytospin samples are prepared by centrifuging the suspensions at 300 rpm for 5 min. To clearly distinguish the eosinophils from the neutrophils, three different stains are applied: Diff-Quick, May-Grunwald-Giemsa, and Hansel (eosin) stains. At least 300 leukocytes are differentiated by light microscopy based on the standard morphologic criteria. The level of IL-13, IL-4 and IL-5 in BALF is detected by Cytometric Bead Assay (BD Biosciences, Mountain View, Calif., USA) following the manufacturer's instructions.

Measurement of serum total IgE and OVA-specific Ig: On day 50, blood samples are obtained from retro-orbital sinus under anesthesia. After the samples had fully coagulated, they are centrifuged, and the sera is collected and stored at −80° C. until use. Total IgE is assayed by ELISA using paired Abs (BD Pharmingen) according to the manufacturer's instructions. To measure OVA-specific IgE, IgG1, and IgG2a in sera, microtiter plates (Maxisorp, Nunc, VWR International, Haasrode, Belgium) are coated with 2 µg/ml OVA. Subsequently, the wells are blocked with 0.1% casein in PBS, after which the plates are incubated with mouse serum samples diluted 1:10 to 1:20480 in PBS containing 0.1% casein and 0.05% TWEEN 20® (PBS-CT), with goat anti-mouse IgG2a-HRP [Southern Biotechnology Associates (SBA), Imtec ITK Diagnostics, Antwerpen, Belgium, dilution 1:5000], goat anti-mouse IgG1-HRP or goat anti-mouse IgE-HRP (SBA, dilution 1:5000). After washing, substrate [3,3',5,5' tetramethylbenzidine (TMB) substrate reagent, Pharmingen, Becton Dickinson, Erembodegem, Belgium] is added to each well. Finally, reactions are stopped by adding $1M\ H_2SO_4$ to the wells. The absorbances are read at 450 nm. ELISA scores are expressed as titers, which are the inverse of the highest dilution that still had on ($OD_{450}$ higher than the calculated cutoff value. The cutoff is calculated as the mean $OD_{450}$ of 5 non-immunized mice increased with three times the SD.

Histological examination of lung tissue: After bronchoalveolar lavage samples are obtained, the lungs are perfused with physiologic saline and are resected from the mice. The lungs are fixed with neutralized buffered formalin and embedded in paraffin. Sections (3-µm thick) are stained with H&E or periodic acid-Schiff (PAS). The intensity of histological changes in the lungs is evaluated with four grading scores (0, no inflammation; 1, slight/mild; 2, moderate; and 3, severe), according to the distribution and intensity of the following findings: 1) epithelial shedding or undulation of the nuclei of bronchial epithelial cells, 2) increase in the number of goblet cells, 3) infiltration of inflammatory cells from vessels into the mucosal and submucosal area of the bronchus and peribronchial interstitium, and 4) hypertrophy and thickening of the smooth-muscle cell layer.

RT-PCR for analysis of cytokine and chemokine gene expression in the lung: The lungs are removed after perfusion with physiologic saline, and total RNA is extracted using ISOGEN (Nippon Gene) according to the manufacturer's instructions. Total RNA (10 µg) is reverse-transcribed using oligo(dT)15 primer (Promega) and Superscript II RNase H-reverse transcriptase (Invitrogen Life Technologies) at 42° C. for 2 h. To ensure that each sample contained the same amount of cDNA, the β-actin cDNA concentration of each sample is first determined using β-actin-specific primers. These samples are amplified for the appropriate number of cycles, such that the amount of PCR product remained on the linear part of the amplification curve. The PCR products are electrophoresed in a 2% agarose gel and were visualized by ethidium bromide staining. The levels of IL-13, eotaxin, IL-10, IFN-γ, and TGF-β are determined using the following specific primer sets. TABLE-US-00003 The sense primer for β-actin 5'-ACGACATGGAGAAGATCTGG-3', (SEQ ID NO: 19) and the antisense primer 5'-TCGTAGATGGGCA-CAGTGTG-3'. (SEQ ID NO: 20) The sense primer for IL-13 5'-TCTTGCTTGCCTTGGTGGTCTCGC-3', (SEQ ID NO: 21) and the antisense primer 5'-GATGGCATTGCAATTGGAGAT-GTTG-3'. (SEQ ID NO: 22) The sense primer for eotaxin 5'-GGGCAGTAACTTCCATCTGTCTCC-3', (SEQ ID NO: 23) and the antisense primer 5'-CACTTCTTCTTGGGGT-CAGC-3'. (SEQ ID NO: 24) The sense primer for IL-10

5'-TACCTGGTAGGAGTGATGCC-3', (SEQ ID NO: 25) and the antisense 5'-GCATAGAAGCATACATGATG-3'. (SEQ ID NO: 26) The sense primer for IFN-γ 5'-CATAGAT-GTGGAAGAAAAGA-3', (SEQ ID NO: 27) and the antisense 5'-TTGCTGAAGAAGGTAGTAAT-3'. (SEQ ID NO: 28) The sense primer for TGF-β 5'-CTTTAGGAAGGAC-CTGGGTT-3', (SEQ ID NO: 29) and the antisense 5'-CAG-GAGCGCACAATCATGTT-3'. (SEQ ID NO: 30)

Cell cultures, proliferation and cytokine assay: One day after the final inhalation (day 50) single cell suspensions of spleen and mediastinal lymph nodes are prepared by passing the cells through 70 μm filter cell strainers (Becton/Dickinson Labware). Erythrocytes are removed from the spleen cell suspensions by incubation with red cell lysis buffer. $CD4^+$ T cells and $CD4^+CD25^-$ T cells are enriched using $CD4^+$ T cell isolation kit (Miltenyi Biotec, Germany) or $CD4^+CD25^+$ regulatory T cell isolation kit (Miltenyi Biotec, Germany), respectively and MACS columns (midiMACS; Miltenyi Biotec).

Proliferation assays of bulk splenocyte and LN populations, $2\times10^5$ cells are cultured in 96-well U-bottom plates in a total volume of 200 μl complete medium either alone or with purified OVA. OVA is added at concentrations ranging from 1 to 100 μg/ml. For proliferation assays of $CD4^+$ T cells and $CD4^+CD25^-$ T cell populations, $2\times10^5$ cells $CD4^+$ T cells or $CD4^+CD25^-$ T cells are cultured in 96-well U-bottom plates with mitomycin treated splenocytes that are loaded with 1 mg/ml OVA for 16 h, acting as antigen presenting cells, at ratio's $CD4^+$ T cell or $CD4^+CD25^-$ T cell/APCs 1/1, 1/0.3, 1/0.1, 1/0.03, 1/0 in a total volume of 200 μl complete medium. After 72 h at 37° C. in a 5% $CO_2$ humidified incubator, proliferation is assessed by addition of 1 μCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis is performed. Cytokine production is quantified using the Mouse Inflammation Cytometric Bead Array (BD Biosciences, Mountain View, Calif., USA).

In vivo T regulatory activity assay: One day after the final inhalation (day 21), spleens of the treated mice are digested with 0.1% collagenase (Sigma-Aldrich) at 37° C. for 20 min. In some experiments, single-cell suspensions of whole spleen cells are prepared and cultured with Con A (2 μg/ml; Sigma-Aldrich) for 48 h. Cells are collected, and $10^7$ cells are adoptively transferred i.v. into naïve BALB/c mice. For negative selection, $CD4^+$, $CD8^+$, $CD11c^+$, $CD19^+$, or $CD11b^+$ cells are depleted from the whole spleen cells using magnetic beads (MACS; Miltenyi Biotec) with biotinylated anti-mouse CD4, CD8, CD11c, CD19, and CD11b mAb (BD Pharmingen), according to the manufacturer's instructions. The efficiency of depletion is examined by flow cytometry (>99%). $CD4^+$, $CD4^+CD25^-$ cells are purified using $CD4^+$ T cell isolation kit. Regulatory T cell isolation kit following the manufacturer's instructions. The purity of positively selected cells is checked using flow cytometry. For cell transfer experiments, cells are transferred into BALB/c mice from the tail veins just before their first immunization or just after their second immunization with OVA/alum. The number of transferred cells is $10^7$ for whole spleen cells, subpopulation-depleted spleen cells, or positively selected $CD4^+$ cells and $CD4^+CD25^-$ cells. In the Humanized SCID (hu-SCID) Model (as Described by Duez et al., 2000; Hammad et al., 2000)

In this model, the allergic immune response to the house dust mite (HDM) allergen Der p 1 can be studied. Such hu-SCID mice reconstituted i.p. with PBMC from HDM-allergic patients and subsequently exposed to aerosols of HDM produce human IgE, develop a pulmonary infiltrate composed of activated T cells and DCs, and exhibit AHR in response to bronchoconstrictor agents (Pestel et al., 1994, J Immunol, 153:3804; Duez et al., Am J Respir Crit. Care Med, vol 161, ppp 200-206, 2000).

Bacteria

The L. lactis strain MG1363 is used throughout this study. Bacteria are cultured in GM17 medium, i.e., M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reached a saturation density of $2\times10^9$ colony-forming units (CFU) per mL within 16 hours. Bacteria are harvested by centrifugation and concentrated 10-fold in BM9 medium. For treatment, each mouse receives 100 μL of this suspension daily by intragastric catheter.

Plasmids

Der p 1, a 222 amino-acid residue globular glycoprotein, is one of the major allergens from Dermatophagoides pteronyssinus (Dpt) mites. DNA sequence with optimal L. lactis codon usage encoding the Der p 1 protein is synthesized, amplified and fused to the Usp45 secretion signal of the erythromycin resistant pT1 NX vector downstream of the lactococcal P1 promotor. MG1363 strains transformed with plasmids carrying murine Der p 1, Der p 1 aa52-71 and Der p 1 aa117-133 cDNA are designated LL-Derp1, LL-Derp1aa52-71 and LL-Derp1aa117-133. LL-pT1 NX, which is MG1363 containing the empty vector pT1 NX, serve as control.

Quantification of Der p 1

Der p 1 from LL-Derp1 is determined using an in house developed Der p 1-specific enzyme-linked immunosorbent assay (ELISA). Production of the recombinant proteins is also assessed by Western blot analysis.

Patients

Blood is collected from donors sensitive or not sensitive to house dust mites. Allergic patients present the usual features of house dust mite sensitization. Skin prick tests toward Dermatophagoides pteronyssinus (Dpt) allergen (Stallergenes, Fresnes, France)(diameter.gtoreq.10 mm) are positive, and all patients have serum specific IgE antibodies. Total IgE concentrations are greater than 150 IU/ml (150-1600 IU/ml). Healthy donors are tested as negative controls (total IgE levels are less than 150 IU/ml, and they have negative skin prick tests toward commonly inhaled allergens).

Human Peripheral Blood Mononuclear Cell Preparation

Platelet rich plasma is obtained after centrifugation (120× g, 15 minutes) and discarded. Blood cells are then diluted in RPMI 1640 (Life Technologies, Paisley, Scotland) (vol/vol) and layered over a Ficoll gradient (Pharmacia, Uppsala, Sweden). After centrifugation (400×g, 30 minutes), PBMCs are harvested at the interface and washed three times in sterile RPMI medium before transfer.

Mice

C.B.-17 SCID mice (6-8 weeks old) are maintained in isolators with sterilized bedding in a specific animal facility. The SCID colony is regularly checked for absence of mouse serum immunoglobulins by ELISA.

Peripheral Blood Mononuclear Cells Transfer in SCID Mice: PBMC hu-SCID Mice

SCID mice are between 6 and 8 weeks old at the time of cell transfer. The mice are reconstituted by intraperitoneal injection of 10×10⁶ mononuclear cells from allergic patients or healthy donors in 400 µl of RPMI via a 23-gauge needle. On the same day, they receive intraperitoneally 2 index reactivity [IR] units Dpt. Four days after the cell reconstitution, SCID mice are exposed to daily allergen aerosols containing 100 IR units of Dpt (100 IR units are equivalent to approximately 200 µg of protein contained in the Dpt extract) for 4 successive days (day 0 to day 4). The control group is not exposed to Dpt. One day before airway responsiveness measurement (day 35 and day 60), hu-SCID mice are exposed to another aerosol of 100 IR units of Dpt solution.

Experimental Setting

Mice receive *L. lactis* engineered to express Der p 1 or an irrelevant antigen (OVA) as negative control.

The engineered *L. lactis* bacteria are administered orally to SCID mice using a gastric catheter, using different treatment intervals and doses starting one day after PBMC reconstitution. Induction of oral tolerance is assessed by measuring human serum IgE antibodies, analysis of pulmonary infiltration, measurement of AHR and analysis of cell populations and cytokine production in the BALF. Furthermore, induction of tolerance is assessed by analysis of the proliferative T cell response against Der p 1.

Assessment of Airway Responsiveness (AHR)

Airway responsiveness (expressed as provocative dose of carbachol causing a 50% increase in lung resistance) is measured on day 35 or day 60 as described by Duez et al., 2000.

Human IgE Measurements

Several days after transplantation with human cells, mice are bled from the retro-orbital sinus under anesthesia. Total human IgE is investigated by a two-site immuno-radiometric method with the use of two different mouse mAbs specific for the E-chain (Immunotech International, Luminy, France). At least 20 µl of serum is used in a duplicate test. The sensitivity of the method permits the detection of 0.1 IU/ml (0.24 ng/ml).

Specific IgE Ab against Dpt allergen is quantified by ELISA. Briefly, plastic tubes (Maxisorb Startube, Nunc, Denmark) are coated overnight with Dpt allergen in 0.1 M carbonate/bicarbonate buffer (pH 9.6) at 4° C. and saturated with 1% BSA in 0.1 M PBS (pH 7.4) for 2 h at room temperature. After washing, the tubes are incubated for 2 h at room temperature and overnight at 4° C. with Hu-SCID mice serum diluted in PBS containing BSA (1%) and TWEEN® (0.01%). After extensive washings, a HRP-labeled anti-human IgE Ab is added. After washing, substrate [3,3',5,5' tetramethylbenzidine (TMB) substrate reagent, Pharmingen, Becton Dickinson, Erembodegem, Belgium] is added to each well. Finally, reactions are stopped by adding 1M $H_2SO_4$ to the wells. The absorbances are read at 450 nm.

Histological Examination of the Lung

Lungs are excised at day 35 and fixed in paraformaldehyde and processed from paraffin embedding. Paraffin tissue sections are stained for the detection of human CD45⁺ cells after which human cells on the murine lung sections were quantified by histological scoring as described by Duez et al., 2000.

Analysis of Bronchoalveolar Lavage Fluid (BALF)

BALF is analyzed as described in the OVA allergen model.

Cell Cultures, Proliferation and Cytokine Assay:

Single cell suspensions of spleen are prepared by passing the cells through 70 µm filter cell strainers (Becton/Dickinson Labware). Erythrocytes are removed from the spleen cell suspensions by incubation with red cell lysis buffer. $CD4^+$ T cells and $CD4^+CD25^-$ T cells are enriched using human $CD4^+$ T cell isolation kit (Miltenyi Biotec, Germany) or human $CD4^+CD25^+$ Regulatory T cell isolation kit (Miltenyi Biotec, Germany), respectively and MACS columns (midi-MACS; Miltenyi Biotec).

Proliferation assays of bulk splenocyte, 2×10⁵ cells are cultured in 96-well U-bottom plates in a total volume of 200 µl complete medium either alone or with purified Der p 1, and either with or without anti-IL-10 or anti-TGF-β neutralising monoclonal antibodies. Der p 1 is added at concentrations ranging from 1 to 100 µg/ml. The neutralizing antibodies are added at 1, 0.1 and 0.01 µg/ml. For proliferation assays of human $CD4^+$ T cells and human $CD4^+CD25^-$ T cell populations, 2×10⁵ cells $CD4^+$ T cells or $CD4^+CD25^-$ T cells are cultured in 96-well U-bottom plates with mitomycin treated human PBMC that are loaded with 1 mg/ml Der p 1 for 16 h, acting as antigen presenting cells, at ratio's $CD4^+$ T cell or $CD4^+CD25^-$ T cell/APCs 1/1, 1/0.3, 1/0.1, 1/0.03, 1/0 in a total volume of 200 µl complete medium either with or without neutralizing antibodies. After 72 h at 37° C. in a 5% $CO_2$ humidified incubator, proliferation is assessed by addition of 1 µCi/well [³H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis is performed. Cytokine production is quantified using the Human Inflammation Cytometric Bead Assay (BD Biosciences, Mountain View, Calif., USA).

Results

LL-OVA and LL-Der p 1 Significantly Enhances the Tolerance-Inducing Capacity in OVA- and huSCID Mice Model for Asthma, Respectively.

To study the induction of oral tolerance, mice are orally fed as described above (experimental setting). Addition of LL-OVA/Derp1 significantly enhances the tolerance induction towards OVA/Derp1 as the allergen-specific proliferative response of the splenocytes is significantly reduced in the LL-OVA/Derp1 group in comparison to the control and free OVA/Derp1 groups. LL-OVA/Derp1 Potentiates Oral Tolerance in Association with Reduced AHR, Eosinophilic Infiltration, Serum IgE Levels, and Lowered IL-13, IL-4 and IL-5 Cytokine Production in Response to Said Allergen.

To study the induction of oral tolerance, mice are orally fed as described above (experimental setting). AHR, eosinophilic BALF infiltration, IgE titer as well as cytokine production in response to said antigens is determined as described above. AHR, eosinophilic BALF infiltration, IgE titer is strongly reduced, and IL-13, IL-4 and IL-5 significantly lowered in the LL-OVA/Derp1 group in comparison to the control and free OVA/Derp1 groups. LL-OVA/Derp1 Enhances Oral Tolerance Via $CD4^+$ T Cells.

To assess whether CD4 T cells mediate the induction of oral tolerance, the allergen-specific proliferative CD4 T-cell response is studied in the splenocytes and lymph nodes. Therefore, mice are orally fed as described above (experimental setting) and the allergen-specific $CD4^+$ T cell proliferation is determined as described in Cell cultures, proliferation and cytokine assay. The allergen-specific CD4 T cell response in the LL-OVA/Derp1 group is significantly reduced in comparison to the control and free-OVA/Derp1 groups.

Antigen-Induced T Regulatory Cells Following LL-OVA Therapy can Transfer Protection from Asthma-Like Responses In Vivo In order to test for active suppression of asthma-like responses in mice treated with the oral tolerance protocol, we adoptively transfer splenocytes from the different treated groups as described above (In vivo T regulatory activity assay). Compared with controls and free OVA groups, asthma-like responses are significantly reduced in the LL-OVA group, indicating activation of regulatory CD4+ T cells in our combination oral tolerance protocol.
Conclusion Our data demonstrate that mucosal delivery of allergen secreting L. lactis is more potent than free allergen to induce allergen-specific immune tolerance via the induction of antigen-specific CD4+ regulatory T cells, even in the setting of established hypersensitivity.

Example E

Induction of Tolerance to BLG Food Allergen Following Oral Administration of L. lactis Secreting Said Allergen Introduction Food allergy is a disease affecting approximately 2% to 5% of the population. In human beings, elevated IgE antibodies as well as the presence of IL-4-producing, antigen-specific T lymphocytes suggest a Th2-skewed mechanism. Here, we demonstrate that oral delivery of a food allergen by L. lactis suppresses allergen-specific immune responses via the induction of antigen-specific CD4+ regulatory T cells.
Material and Methods to the Examples
Bacteria and Plasmids The L. lactis strain MG1363 is used throughout this study. Bacteria are cultured in GM17 medium, i.e., M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reach a saturation density of $2 \times 10^9$ colony-forming units (CFU) per mL within 16 hours. Bacteria are harvested by centrifugation and concentrated 10-fold in BM9 medium. For treatment, each mouse receives 100 μL of this suspension daily by intragastric catheter. Bovine β-lactoglobulin cDNA is amplified and fused to the Usp45 secretion signal of the erythromycin resistant pT1 NX vector, downstream of the lactococcal P1 promotor. MG1363 strains transformed with plasmids carrying murine BLG is designated LL-BLG. LL-pT1 NX, which is MG1363 containing the empty vector pT1 NX, serve as control.
Quantification of Bovine β-Lactoglobulin (BLG)

BLG from LL-BLG is determined using an in house developed BLG-specific enzyme-linked immunosorbent assay (ELISA) and Western blot analysis.
Experimental Setting The murine model of food allergy used to explore the protective effect of L. lactis is a mouse model of food-induced IgE-type response as described by Frossard et al. (J Allergy Clin Immunol 113:958-964, 2004). Mice receive LL-BLG or an irrelevant antigen (OVA) as negative control. As a positive control for tolerance induction, mice receive a high dose of BLG in the drinking water that prevents the mice from anaphylaxis upon oral challenge with BLG.

In a prophylactic setting, the engineered L. lactis bacteria that produce BLG are administered orally to the mice using a gastric catheter, using different treatment intervals and doses. Subsequently, these recipient mice are orally challenged with purified BLG antigen, in the presence of cholera toxin. Control animals are exposed to L. lactis engineered with a control vector that does not express BLG (but OVA instead). Induction of tolerance is assessed by analysis of anaphylaxis after intragastric antigen challenge, by measuring BLG-specific IgG1, IgG2a and IgE titers in serum and faeces, by determining the number of antibody secreting cells in spleen and PP, by analysis of the T cell proliferation and cytokine production in MLN, PP and spleen.

To evaluate whether the induction of immune tolerance towards BLG could be enhanced by L. lactis, mice are administered with LL-BLG or with 1 μg free BLG.
Oral Sensitization to BLG.

Four- to 5-week-old female C3H/HeOuJ mice (Charles River) are immunized at days 0, 7, 14, and 21 by intragastric gavage with 20 mg of BLG (Sigma) and 10 μg of CTX, purchased from List Biological Laboratories in 0.2 mol/L NaHCO.sub.3. The positive control group (tolerized mice) receive 0.8 mg/mL BLG in their drinking water ad libitum for 4 weeks. The total amount of protein given (22.4 mg) is similar to the total amount of BLG given to the sensitized mice. To demonstrate that the tolerization procedure also enduringly activate the peripheral and not only the mucosal immune system, a group of tolerized mice is injected twice with 80 μg ip BLG adsorbed to 1 mg alum at days 28 and 42.
Antigen Challenge On day 28, all mice are challenged by intragastric gavage with 100 mg BLG in 0.4 mL 0.2 mol NaHCO3. Anaphylaxis is observed and graded by using a reaction score (0, no reaction, to 3, severe reaction or death) described in detail elsewhere (Frosssard et al., 2001). The core body temperature is measured by infrared at the ear before challenge and 30 minutes after gavage. The animals are killed, and blood is collected by cardiac puncture into EDTA-containing tubes, and plasma is obtained for histamine measurement by commercial ELISA kit (Immunotech, Marseille, France).
Cell Cultures, Proliferation and Cytokine Assay Single cell suspensions of spleen, mesenteric lymph nodes and PP are prepared as described by Frossard et al. (2004). CD4+ T cells and CD4+CD25− T cells are enriched using CD4+ T cell isolation kit (Miltenyi Biotec, Germany) or CD4+CD25+ Regulatory T cell isolation kit (Miltenyi Biotec, Germany), respectively and MACS columns (midiMACS; Miltenyi Biotec).

Proliferation assays of bulk splenocyte and LN populations, $2 \times 10^5$ cells are cultured in 96-well U-bottom plates in a total volume of 200 μl complete medium either alone or with purified BLG, and either with or without anti-IL-10 or anti-TGF-β neutralising monoclonal antibodies. BLG is added at concentrations ranging from 1 to 100 μg/ml. The neutralizing antibodies are added at 1, 0.1 and 0.01 μg/ml. For proliferation assays of CD4+ T cells and CD4+CD25− T cell populations, $2 \times 10^5$ cells CD4+ T cells or CD4+CD25− T cells are cultured in 96-well U-bottom plates with mitomycin treated splenocytes that are loaded with 1 mg/ml BLG for 16 h, acting as antigen presenting cells, at ratio's CD4+ T cell or CD4+CD25− T cell/APCs 1/1, 1/0.3, 1/0.1, 1/0.03, 1/0 in a total volume of 200 μl complete medium either with or without neutralizing antibodies. After 72 h at 37° C. in a 5% $CO_2$ humidified incubator, proliferation is assessed by addition of 1 μCi/well [$^3$H]-thymidin. DNA-bound radioactivity is harvested 18 h later onto glass fiber filter mats (Perkin Elmer, Boston, USA) and thymidine-incorporation is measured on a scintillation counter (Perkin Elmer).

For cytokine measurements, supernatants of the cell cultures used in the different proliferation assays is collected after 24, 48 and 72 h of culture and frozen at −80° C. until cytokine analysis will be performed. Cytokine production is quantified using the Mouse Inflammation Cytometric Bead Assay (BD Biosciences, Mountain View, Calif., USA).
In Vivo T Regulatory Activity Assay In order to test for active suppression of antibody formation in mice, splenocytes, bead-purified CD4+ T cells, CD4+

CD25⁻ or CD4⁺CD25⁺ T cells isolated from the different experimental *L. Lactis*-treated groups are adoptively transferred to naïve C3H/HeOuJ mice. Untreated mice are used as control. The number of transferred cells is $10^7$ for whole spleen cells, subpopulation-depleted spleen cells, or positively selected CD4⁺ cells and CD4⁺CD25 and CD4⁺CD25⁺ T cells. If Tregs are implicated, subsequent challenge of these mice with BLG antigen should prevent induction of humoral immune responses against BLG and anaphylaxis. Enzyme-Linked Immunoassays for BLG-Specific Serum and Feces Antibodies.

Sera are obtained from tail bleedings at day 0, 7, 14, 21 and 28. Feces are obtained at the same times and resuspended in PBS plus 1% FCS (Life technologies) supplemented with pepstatin 1:1000 (Fluka) at 0.1 mg/mL. The samples are mechanically disaggregated and vortexed for 2 minutes, followed by two centrifugations at 4° C. for 20 minutes at 14,000 rpm.

Sera and feces are assayed for BLG-specific IgE, IgG1, IgG2a and/or IgA antibody levels by a method adapted from Adel-Patient et al. (2000, J. Immunol. Methods). In brief, MaxiSorp microtiter plates (Nunc) are coated for 18 hours at room temperature with 250 ng/well streptavidin (Fluka), followed by 300 μL of a solution of polyvinylpyroliddon K25 (Fluka) overnight. One microgram of biotinylated BLG is incubated for 3 hours, and diluted sera (1:6666 and 1:2222 for IgG1, 1:666 and 1:222 for IgG2a, 1:66 and 1:22 for IgE) or feces (1:3, 1:10, and 1:33) in PBS plus 10% horse serum is added in duplicates in presence of 0.5 μg/mL goat anti-mouse IgA, rat anti-mouse IgG1 or anti-mouse IgG2a peroxidase-labeled antibodies (Southern Biotechnologies) for 2 hours. For IgE measurement, a monoclonal rat anti-mouse IgE Ab (clone R35-72, BD Pharmingen) followed by peroxidase-coupled anti-rat Ab (Caltag) is added. Optical density is measured at 490 nm. Results are expressed as arbitrary units, with pooled sera from BLG plus alumimmunized mice used as a reference serum.

Antigen-Specific Antibody Production is Measured by Means of ELISPOT.

Peyer's patches are excised mechanically from the gut and incubated for 30 minutes in HBSS medium supplemented with 5 mmol EDTA (Life Technologies). Similarly, Peyer patches and mesenteric lymph nodes are gently crushed and filtered through a 70-m nylon filter. Spleen cells are preincubated for 5 minutes in Tris-buffered NH.sub.4C1 to remove red blood cells. Lymphoblasts are isolate on a Percoll 60%/66% gradient (Amersham).

For the measurement of BLG-specific IgG1, IgG2a and IgA antibodies, ELISPOT plates (Millipore) are coated with streptavidin overnight at 37° C., followed by addition of 1 g of biotinylated BLG for 3 hours. Lymphoblasts isolated on a Percoll 60%l66% gradient from are resuspended at two different concentrations, 1 and $2\times10^6$ in Iscove's modified Dulbecco's medium supplemented with penicillin, streptomycin, L-glutamine, gentamicin, polymixin B, and 5% FCS for 24 hours at 37° C., followed by overnight incubation at 4° C. with anti-IgA, anti-IgG1 and anti-IgG2a antibodies (Southern Biotechnology). Amino-ethyl-carbazole, 100 μL/well, is added for 10 minutes, and the spots are automatically counted by using the KS ELISPOT 4.2.1 Software (Zeiss) and expressed as cell-forming units per $10^6$ cells (CFU).

LL-BLG Significantly Enhances the Tolerance-Inducing Capacity of BLG in Murine Model of Food Allergy To study the induction of oral tolerance, mice are orally fed as described above (experimental setting). Addition of LL-BLG significantly enhances the tolerance induction towards BLG as the allergen-specific proliferative response of the splenocytes is significantly reduced in the LL-BLG group in comparison to the control and free-BLG groups.

LL-BLG potentiates oral tolerance in association with reduced BLG-specific antibody response and lowered IL-4 cytokine production in response to said allergen.

To study the induction of oral tolerance, mice are orally fed as described above (experimental setting). BLG-specific antibody response and cytokine production in response to said factor is determined as described above. BLG-specific antibodies levels and IL-4 are significantly lowered in the LL-BLG group in comparison to the control and free-BLG groups.

Results

LL-BLG Enhances Oral Tolerance Via CD4⁺ T Cells.

To assess whether CD4 T-cells mediate the induction of oral tolerance, the allergen-specific proliferative CD4 T-cell response is studied in the splenocytes and lymph nodes. Therefore, mice are orally fed as described above (experimental setting) and the allergen-specific CD4⁺ T cell proliferation is determined as described in Cell cultures, proliferation and cytokine assay. The allergen-specific CD4 T-cell response in the LL-BLG group is significantly reduced in comparison to the control and free-BLG groups.

Antigen-Induced T Regulatory Cells Following
LL-BLG Therapy can Transfer Protection from
Allergic-Like Responses In Vivo In order to test for active suppression of allergic-like responses in mice treated with the oral tolerance protocol, we adoptively transfer splenocytes from the different treated groups as described above (In vivo T regulatory activity assay). Compared with controls and free-BLG groups, allergic-like responses are significantly reduced in the LL-BLG group, indicating activation of regulatory CD4⁺ T cells in our combination oral tolerance protocol.

Conclusion

Our data demonstrate that mucosal delivery of allergen secreting *L. lactis* is more potent than free allergen to induce allergen-specific immune tolerance via the induction of antigen-specific CD4⁺ regulatory T cells.

Example F

Induction of Tolerance to Insulin Following Oral
Administration of *L. lactis* Secreting Said
Autoantigen Introduction Autoimmunity is characterized by spontaneous inflammatory tissue damage and by impaired physiological function resulting from loss of tolerance to self-antigen. It is associated with a partially overactive immune system, which is characterized by an excess of T helper (Th) cells. Predisposing factors, such as susceptibility genes and environmental factors are difficult to influence, therefore recent efforts to develop immunotherapies are focused on re-establishing the functional balance between pathogenic effector cells and immunoregulatory T cells by depleting the former and/or enhancing the latter. Autoimmune destruction of pancreatic islet beta cells is the major cause of Type 1 diabetes mellitus (T1D). This destruction is associated with cellular and humoral immune responses to several beta cell autoantigens, both of which can precede the clinical onset of disease.

Here, we demonstrate that oral delivery of an autoantigen delivering *L. lactis* suppresses diabetic-specific immune responses via the induction of antigen-specific CD4⁺ regulatory T cells.

Material and Methods

Bacteria and Plasmids

The *L. lactis* strain MG1363 is used throughout this study. Bacteria are cultured in GM17 medium, i.e., M17 (Difco Laboratories, Detroit, Mich.) supplemented with 0.5% glucose. Stock suspensions of all strains are stored at −20° C. in 50% glycerol in GM17. For intragastric inoculations, stock suspensions are diluted 200-fold in fresh GM17 and incubated at 30° C. They reach a saturation density of $2\times10^9$ colony-forming units (CFU) per mL within 16 hours. Bacteria are harvested by centrifugation and concentrated 10-fold in BM9 medium. For treatment, each mouse receives 100 μL of this suspension daily by intragastric catheter. DNA sequence with optimal *L. lactis* codon usage encoding the human proinsulin II B24-C36 peptide (hpIIp), porcine insulin and immunodominant-peptide $InsB.9-23$ (B9-23 is essentially the same across many species human, rat and mouse) are synthesized, amplified and fused to the Usp45 secretion signal of the erythromycin resistant pT1NX vector, downstream of the lactococcal P1 promotor.

MG1363 strains transformed with plasmids carrying murine hpIIp, Insulin, $InsB.9-23$ are designated LL-hpIIp, LL-insulin, $LL-InsB.9-23$. LL-pT1NX, which is MG1363 containing the empty vector pT1NX, served as control. Expression of these proteins is determined using antigen-specific ELISA and Western blot analysis.

Mice

Non-obese female and male diabetic (NOD) mice and NOD-severe combined immunodeficient (SCID) (Balb/c background) mice are purchased from the Jackson laboratory. Balb/c wild type (WT) mice are purchased from Charles River Italy. Mice are maintained in a specific pathogen-free central animal facility. Mice are treated and used in agreement with the institutional guidelines.

Experimental Setting

In a prophylactic setting, the LL-hpIIp, LL-insulin, $LL-InsB.9-23$ are administered orally to NOD mice starting from day 21 of age (weaning), and using the optimal feeding regime or until 100 days of age (when most mice develop diabetes). In addition, LL-pT1NX is administered orally as a negative control. For the positive (tolerizing) control group, 3-week-old NOD mice are treated orally with 0.8 mg human insulin/hpIIp/$InsB.9-23$ for 3 times a week for 2 or 4 weeks. Development of diabetes is determined by continuous monitoring of urine glucose levels three times a week and in case of glucosuria monitoring of blood glucose levels. Pancreases are collected at 12-23 weeks and at the end of experiment (35 weeks), and serial sections are stained with hematoxylin/eosin to score mononuclear cell infiltration or by immunohistochemistry to analyse T cell infiltration.

In a therapeutic setting the LL-hpIIp, LL-insulin, $LL-InsB.9-23$ are administered orally to diabetic NOD females showing stable glycosuria and hyperglycemia (12-23 weeks). In addition, LL-pT1 NX is administered orally as a negative control. For the positive (tolerizing) control group, diabetic NOD mice are treated as described in Bresson et al., 2006. Complete remission is defined as the disappearance of glycosuria and a return to normal glycemia.

In a syngeneic islet transplantation setting, female NOD mice with recent-onset diabetes are treated orally for 3 weeks with LL-hpIIp, LL-insulin, $LL-InsB.9-23$, or with LL-pT1 NX as a negative control. After 3 weeks, 500 freshly isolated pancreatic islets from non-diabetic NOD mice are transplanted to diabetic NOD mice. Blood glucose is then monitored 3 times weekly until diabetes recurrence or until 15 weeks after grafting. Animals with 2 consecutive glucose levels 250 mg/dL are considered diabetic and will be subsequently killed for serum collection and histological analysis of the graft.

The precise mechanisms of tolerance induction are analyzed in vitro, in vivo after re-challenging the NOD mice with specific autoantigens and by adoptive T-cell transfer into NOD-SCID mice.

Detection of Diabetes:

Glucose monitoring: urine glucose is measured by using Diastix (Miles) and is confirmed by blood glucose measurements with the blood glucose monitoring system OneTouch Ultra (LifeScan Inc.). Diabetes is defined as 2 consecutive blood glucose values superior to 250 mg/dl.

Insulitis: Mice are killed by $CO_2$ asphyxiation and the pancreas is fixed in 10% formalin overnight, embedded in paraffin, and serial 5 μm sections are stained with haematoxylin and eosin. The insulitis score (mean±SD) is determined by microscopically grading the degree of cellular infiltration in 10-15 islets/mouse as follows: 0, no visible sign of islet infiltration; 1, peri-islet infiltration; 2, <50% infiltration; 3, >50% infiltration.

Islet isolation and transplantation: Islets of insulitis- and diabetes-free 14- to 21-day old donor NOD mice are isolated after aseptic removal by digesting the pancreatic glands with collagenase in Hanks' balanced salt solution during vigorous shaking Islet isolation is carried out by direct hand-picking under a stereo-microscope. Diabetic recipient NOD mice were anaesthetized by intraperitoneal injection of avertin (0.02 ml/g BWT), the left kidney was exposed via lumbar incision and 500 freshly isolated islets were given under the renal capsule.

Immunohistochemistry

To detect insulin, CD4 and CD8 expression in pancreatic R cells, primary Abs (guinea pig anti-swine insulin from Dako [dilution 1:300], anti-CD4 RM4.5 and anti-CD8a IHC from BD Biosciences [dilution 1:50] are applied to frozen tissue sections as described in Christen et al., 2004.

In Vitro Proliferation Assay

Single cell suspensions of spleen, mesenteric LN (MLNs) and PLNs are prepared. Proliferation assays of total splenocyte populations, $2\times10^5$ cells are cultured in 96-well U-bottom plates in a total volume of 200 μl complete medium either alone or with graded concentrations (1-100 μg/ml) of purified human insulin or peptides specific for CD4 T cells ($InsB.9-23$, $H-2^d$ or g restricted) or for CD8 T cells ($InsB.15-23$, $K^d$ restricted) (Sigma), and either with or without anti-IL-10 or anti-TGF-β neutralising monoclonal antibodies. The neutralizing antibodies are added at 1, 0.1 and 0.01 μg/ml. For proliferation assays of total $CD3^+$ T cells, $CD8^+$ T cells, $CD4^+$ T cells and $CD4^+CD25^-$ T cell populations, $0.2\times10^5$ cells T cells are cultured in 96-well U-bottom plates with $1\times10^5$ irradiated splenocytes from WT Balb/c mice loaded with insulin or GAD65 or peptides specific for $CD4^+$ or $CD8^+$ T cells, in a total volume of 200 μl complete medium either with or without neutralizing antibodies. After 72 hr at 37° C. in a 5% $CO_2$ humidified incubator, proliferation is assessed by addition of 1 μCi/well [$^3$H]-thymidin. DNA-bound radioactivity is harvested 16-18 hr later onto glass fiber filter mats (Perkin Elmer, Boston, USA) and thymidine-incorporation is measured on a scintillation counter (Perkin Elmer). T-cells are purified from PLNs or spleens by negative selection through magnetic bead separation using $CD3^+$, $CD4^+$ or $CD8^+$ isolation kit (MACS; Milteny Biotec, Auburn, Calif.). $CD4^+$ T cells are used as total cells or further separated into $CD25^+$ and $CD25^-$ by MACS using $CD25^+$ isolation kit (Milteny Biotec). The purity (>90%) of the cell populations is determined by flow cytometric analysis.

For cytokine measurements, supernatants of the cell cultures used in the different proliferation assays (antigen-specific stimulation), described above, are collected after 72 h of culture and frozen at −80° C. until cytokine analysis is performed. Cytokine production is quantified using the Mouse Inflammation Cytometric Bead Assay (BD Biosciences, Mountain View, Calif., USA). Purified CD3$^+$ T cells, CD4$^+$ T or CD8$^+$ T cells are cultured and stimulated in vitro non-specifically with an anti-CD3/anti-CD28 mixture (1 µg/ml each) for 24 hours or they remain unstimulated as control. The supernatants is harvested, and analysed for IL-10, IL-4, IL-5 and IFNγ production using BD™ Cytometric Bead Array flex set on a BD FACSArray Bioanalyzer using the FCAP array software (BD Biosciences). Capture ELISA experiments are used to determine TGF-β1 using the Quantikine kit (R&D Systems).

In Vitro T Cell Proliferation Inhibition Assay $2 \times 10^4$ purified total splenic CD4$^+$CD25$^-$ T cells isolated from recently diabetic female NOD (8-12 weeks) are co-cultured with varying numbers of CD8$^+$ T cells, CD4$^+$ T cells and CD4$^+$CD25$^-$ T cell populations isolated from the spleen, MLN or PLNs from the different experimental groups in the presence of $2 \times 10^4$ T-cell depleted irradiated insuline- or petides-loaded splenocytes from WT Balb/c mice. After 72 hr at 37° C. in a 5% CO$_2$ humidified incubator, proliferation is assessed by addition of 1 µCi/well [$^3$H]-thymidin. DNA-bound radioactivity is harvested 16-18 hr later onto glass fiber filter mats (Perkin Elmer, Boston, USA) and thymidine-incorporation measured on a scintillation counter (Perkin Elmer).

In Vitro Cytotoxicity Assay

Lymphoblast targets used are Con A-activated splenocytes from BALB/c mice. A total of $10^6$ target cells are labelled with 100 µCi of $^{51}$Cr (Amersham International, Buckinghamshire, U.K) for 90 min at 37° C., washed three times and then incubated with 1 µg/ml peptide (InsB.sub.15-23 or an irrelevant peptide) at 37° C. for 1 h. Target cells are washed two times and seeded at $10^4$ cells per well. CD8$^+$ T cells, isolated from spleen, MLNs and PLNs are added to each well, in triplicate, at various effector:target (E:T) ratios. The plates are centrifuged at 500 rpm for 2 min, and incubated at 37° C. for 4 h. After incubation, supernatants are collected for determination of $^{51}$Cr release [% lysis=100×(test cpm-spontaneous cpm)/(total cpm-spontaneous cpm)]. For the indirect killing assay, CD8$^+$ T cells are incubated with 5 µg/ml anti-CD3 antibody (clone 145-2C11, Pharmingen) prior to incubation with effectors.

Adoptive Transfer of Diabetes

NOD-SCID mice at 8-10 wk are injected i.v. with $2 \times 10^7$ or i.p. with $5 \times 10^6$ splenocytes isolated from diabetic female NOD mice (6 weeks, 12 weeks and 18 weeks) combined with or without graded numbers of bead-purified CD3$^+$ T cells, CD8$^+$ T cells, CD4$^+$ T cells, CD4$^+$CD25$^-$ or CD4$^+$CD25$^+$ T cells isolated from the different experimental *L. Lactis*-treated groups. Untreated mice are used as control. Development of diabetes is determined by continuous monitoring of blood glucose levels three times a week.

Results

LL-hpIIp, LL-Insulin, LL-InsB.sub.9-23 Delays Diabetes Recurrence After Syngeneic Islet Transplantation To assess whether LL-hpIIp, LL-Insulin and LL-InsB(9-23) induce oral tolerance, diabetes recurrence after syngeneic islet transplantation is studied. Therefore, mice are orally fed as described above (experimental setting) and pancreatic islets are transplanted as described (Islet isolation and transplantation). Diabetes recurrence is delayed in the LL-hpIIp/insulin/InsB.sub.9-23 group in comparison to the control.

LL-hpIIp, LL-insulin, or LL-InsB.sub.9-23 significantly enhances the tolerance-inducing capacity of freehpIIp, insulin, or InsB.sub.9-23 in the non-obese diabetic mouse To study the induction of oral tolerance, mice are orally fed as described above (experimental setting). Addition of LL-hpIIp, LL-insulin, LL-InsB.sub.9-23 significantly enhances the tolerance induction towards autoantigen as the autoantigen-specific proliferative response of the splenocytes is significantly reduced in the LL-hpIIp/insulin/InsB.sub.9-23 group in comparison to the control and free hpIIp/insulin/InsB.sub.9-23 groups.

LL-hpIIp, LL-insulin, or LL-InsB.sub.9-23 potentiates oral tolerance in association with reduced insulitis, deceased rate of beta cell destruction, and increased IL-10 production by splenocytes To study the induction of oral tolerance, mice are orally fed as described above (experimental setting). The presence of insulitis, the rate of beta-cell destruction and cytokine production in response to said autoantigen is determined as described above. Histological analysis shows a significant lower degree of insulitis and beta cell destruction and increased IL-10 production in the LL-hpIIp/insulin/InsB.sub.9-23 group in comparison to the control and free-hpIIp/insulin/InsB.sub.9-23 groups.

LL-hpIIp, LL-Insulin, LL-InsB.sub.9-23 Enhances Oral Tolerance Via CD4$^+$ T Cells To assess whether CD4 T cells mediate the induction of oral tolerance, the autoantigen-specific proliferative CD4 T-cell response is studied in the splenocytes and lymph nodes. Therefore, mice are orally fed as described above (experimental setting) and the autoantigen-specific CD4$^+$ T cell proliferation is determined as described (in vitro proliferation assay). The autoantigen-specific CD4 T cell response in the LL-hpIIp/insulin/InsB.sub.9-23 group in comparison to the control and free-hpIIp/insulin/InsB.sub.9-23 groups.

Example F5

Autoaggressive CD8$^+$ Responses are Suppressed in NOD Mice Following LL-InsB.sub.9-23 Therapy To examine whether our combination approach induce suppressive CD4$^+$ T cells that are capable of modulating diabetes by bystander suppressive mechanisms, we analyze the effect on CD8$^+$ autoaggresive T cells. The percentage and/or activity of antigen-specific autoaggressive CD8$^+$ cells is strongly reduced after LL-InsB.sub.9-23 therapy.

Antigen-Induced T Regulatory Cells Following LL-InsB.sub.9-23 Therapy can Transfer Protection from Autoimmune-Like Responses In Vivo In order to test for active suppression of diabetic-like responses in mice treated with the oral tolerance protocol, we adoptively transfer splenocytes from the different treated groups as described above (adoptive transfer of diabetes). Compared with controls and free-InsB.sub.9-23 group, diabetic-like responses are significantly reduced in the LL-InsB.sub.9-23 group, indicating activation of regulatory CD4$^+$ T cells in our combination oral tolerance protocol.

Conclusion

We demonstrate that oral delivery of an autoantigen delivering *L. lactis* suppresses diabetic-specific immune responses via the induction of antigen-specific CD4$^+$ regulatory T cells.

Discussion

On the whole, the above presented data indicates that oral supplementation of a genetically modified *L. lactis* secreting antigens can decrease systemic inflammation induced by that antigen, even in a sensitized subject. Advantageously, the *Lactococcus*-mediated suppression often appears more potent than after mucosal administration of free antigen. Potentially, the suppression may be mediated by the induction of Foxp3$^+$ regulatory T cells, References Friedman A. and Weiner, H. L. (1994). Induction of anergy or active suppression following oral tolerance is determined by antigen dosage. Proc. Natl. Acad. Sci, 91, 6688-6692.

Gasson, M. J. Plasmid complements of *Streptococcus lactis* NCDO 712 and other lactic streptococci after protoplast-induced curing. J. Bacteriol. 154, 1-9 (1983).

Liu, et al., (2006) Engineered vaginal *Lactobacillus* strain for mucosal delivery of the human immunodeficiency virus inhibitor Cyanovirin-N. A.A.C. 50, 3250-3259.

Marietta, E. et al. A new model for dermatitis herpetiformis that uses HLA-DQ8 transgenic NOD mice. J. Clin. Invest 114, 1090-1097 (2004).

Mayer, L. and Shao, L. (2004a). The use of oral tolerance in the therapy of chronic inflammatory/autoimmune diseases. J. Pediatr. Gastroenterol. Nutr. 39, S746-S747.

Mazzarella, G. et al. An immunodominant DQ8 restricted gliadin peptide activates small intestinal immune response in in vitro cultured mucosa from HLA-DQ8 positive but not HLA-DQ8 negative coeliac patients. Gut 52, 57-62 (2003).

Mucida, D., Kutchukhidze, N., Erazo, A., Russo, M., Lafulle, J. J. and Curotto de Lafulle, M. A. (2005). Oral tolerance in the absence of naturally occurring Tregs. J. Clin. Invest. 115, 1923-1933.

Steidler, L. and Rottiers, P. (2006) Therapeutic drug delivery by genetically modified *Lactococcus lactis*. Ann N Y Acad. Sci. 1072, 176-186.

Strobel, S., Mowat, A. M., Drummond, H. E., Pickering, M. G. and Ferguson, A. (1983) Immunological responses to fed protein antigens in mice. II oral tolerance for CMI is due to activation of cyclophosphamide-sensitive cells by gut-processed antigen. Immunology, 49, 451-456.

Tobagus, I. T., Thomas, W. R., & Holt, P. G. Adjuvant costimulation during secondary antigen challenge directs qualitative aspects of oral tolerance induction, particularly during the neonatal period. J. Immunol. 172, 2274-2285 (2004).

Van Asseldonk, M. et al. Cloning of Usp45, A Gene Encoding A Secreted Protein from *Lactococcus*-Lactis Subsp *Lactis* Mg1363. Gene 95, 155-160 (1990).

Waterfield, N. R., Lepage, R. W. F., Wilson, P. W., & Wells, J. M. The Isolation of Lactococcal Promoters and Their Use in Investigating Bacterial Luciferase Synthesis in *Lactococcus*-Lactis. Gene 165, 9-15 (1995).

---

What is claimed is:

1. A method of treating celiac disease in a subject comprising mucosally delivering a composition to the subject, wherein the composition comprises a genetically engineered *Lactococcus lactis* constitutively expressing and secreting an α-gliadin peptide or a hordein peptide, each peptide comprising a HLA-DQ2-specific epitope or a HLA-DQ8-specific epitope, wherein the composition is delivered mucosally to the subject at least once a day.

2. The method of claim 1, wherein the method results in the induction of regulatory T (Treg) cells.

3. The method of claim 2, wherein the Treg cells are Foxp3+cells.

4. The method of claim 1, wherein the epitope is an immune dominant deamidated epitope.

5. The method of claim 1, wherein the peptide comprises SEQ ID NO: 2, SEQ ID NO: 4, SEQ ID NO: 6, or SEQ ID NO: 8.

6. The method of claim 1, wherein the composition is delivered orally.

7. The method of claim 6, wherein the orally delivered *Lactococcus lactis* composition suppresses gliadin-specific immune responses in the subject.

8. The method of claim 1, wherein the mucosal delivery of the composition is performed for at least one week.

9. The method of claim 1, wherein the mucosal delivery of the composition is performed at least once a day.

10. The method of claim 9, wherein the mucosal delivery of the composition is performed at least twice a day.

11. The method of claim 1, wherein the *Lactococcus lactis* is delivered at a dose of at least 10 femtograms to 500 micrograms daily.

12. The method of claim 1, wherein the composition is delivered as a capsule, tablet, liquid, suspension, emulsion, or troche.

13. The method of claim 1, wherein the composition is formulated as a medicament, medical food, or a neutraceutical.

14. The method of claim 1, wherein a single dose of the composition comprises at least ten femtograms of the *Lactococcus lactis*.

15. The method of claim 1, wherein the peptide is expressed and secreted for the continuous presence at the intended mucosal site.

* * * * *

UNITED STATES PATENT AND TRADEMARK OFFICE
CERTIFICATE OF CORRECTION

PATENT NO. : 8,524,246 B2  Page 1 of 1
APPLICATION NO. : 13/720967
DATED : September 3, 2013
INVENTOR(S) : Pieter Rottiers and Veerle Snoeck It is certified that error appears in the above-identified patent and that said Letters Patent is hereby corrected as shown below:

On the title page:

In ITEM (54) AND IN THE SPECIFICATION, COLUMN 1, LINES 1-4, TITLE    change "TREATMENT OF IMMUNE DISEASE BY MUCOSAL DELIVERY OF ANTIGENTS USING GENETICALLY MODIFIED *LACTOBACILLUS*" to --TREATMENT OF IMMUNE DISEASE BY MUCOSAL DELIVERY OF ANTIGENS USING GENETICALLY MODIFIED *LACTOCOCCUS*--

In ITEM (56) References Cited:
OTHER PUBLICATIONS
Page 2, $2^{nd}$ column, $2^{nd}$ line of the
 $16^{th}$ entry (line 28),    change "epiderinal" to --epidermal--
OTHER PUBLICATIONS
Page 3, $1^{st}$ column, $2^{nd}$ line of the
 $11^{th}$ entry (line 20),    change "Ouse" to --House--
OTHER PUBLICATIONS
Page 4, $1^{st}$ column, $1^{st}$ line of the
 $9^{th}$ entry (line 19),    change "Croh's," to --Crohn's,--

In the specification:
COLUMN 12, LINE 8,   change "gaa" to --gaa--
COLUMN 12, LINE 9,   change "gaa" to --gaa--
COLUMN 12, LINE 14,  change "gaa" to --gaa--
COLUMN 12, LINE 15,  change "gaa" to --gaa--

In the claims:
CLAIM 3, COLUMN 55, LINE 56,   change "Foxp3+cells." to --Foxp3$^+$ cells.--

Signed and Sealed this
Eleventh Day of March, 2014

Michelle K. Lee
*Deputy Director of the United States Patent and Trademark Office*

SEQUENCE LISTING

```
<160> NUMBER OF SEQ ID NOS: 31

<210> SEQ ID NO 1
<211> LENGTH: 54
<212> TYPE: DNA
<213> ORGANISM: artificial sequence
<220> FEATURE:
<223> OTHER INFORMATION: DNA sequence coding for deamidated DQ8 epitope

<400> SEQUENCE: 1
caatacccat caggtgaagg ttcattccaa ccatcacaag aaaacccaca agct          54

<210> SEQ ID NO 2
<211> LENGTH: 18
<212> TYPE: PRT
<213> ORGANISM: artificial sequence
<220> FEATURE:
<223> OTHER INFORMATION: deamidated DQ8 epitope

<400> SEQUENCE: 2

Gln Tyr Pro Ser Gly Glu Gly Ser Phe Gln Pro Ser Gln Glu Asn Pro
1               5                   10                  15

Gln Ala

<210> SEQ ID NO 3
<211> LENGTH: 54
<212> TYPE: DNA
<213> ORGANISM: artificial sequence
<220> FEATURE:
<223> OTHER INFORMATION: DNA sequence coding for Triticum DQ8 epitope

<400> SEQUENCE: 3
```

```
caatacccat caggtcaagg ttcattccaa ccatcacaac aaaacccaca agct          54
```

```
<210> SEQ ID NO 4
<211> LENGTH: 18
<212> TYPE: PRT
<213> ORGANISM: artificial sequence
<220> FEATURE:
<223> OTHER INFORMATION: Triticum DQ8 epitope

<400> SEQUENCE: 4
```

Gln Tyr Pro Ser Gly Gln Gly Ser Phe Gln Pro Ser Gln Gln Asn Pro
1               5                   10                  15

Gln Ala

```
<210> SEQ ID NO 5
<211> LENGTH: 90
<212> TYPE: DNA
<213> ORGANISM: artificial sequence
<220> FEATURE:
<223> OTHER INFORMATION: DNA sequence coding for deamidated DQ2 epitope

<400> SEQUENCE: 5
```

```
ttacaattac aaccattccc acaaccagaa ttaccatacc cattaccata cccacaacca   60
gaattaccat acccacaacc acaaccattc                                    90
```

```
<210> SEQ ID NO 6
<211> LENGTH: 33
<212> TYPE: PRT
<213> ORGANISM: artificial sequence
<220> FEATURE:
<223> OTHER INFORMATION: deamidated DQ2 epitope

<400> SEQUENCE: 6
```

Leu Gln Leu Gln Pro Phe Pro Gln Pro Glu Leu Pro Tyr Pro Gln Pro
1               5                   10                  15

Gln Leu Pro Tyr Pro Gln Pro Glu Leu Pro Tyr Pro Gln Pro Gln Pro
            20                  25                  30

Phe

```
<210> SEQ ID NO 7
<211> LENGTH: 90
<212> TYPE: DNA
<213> ORGANISM: artificial sequence
<220> FEATURE:
<223> OTHER INFORMATION: DNA sequence coding for Triticum DQ2 epitope

<400> SEQUENCE: 7
```

```
ttacaattac aaccattccc acaaccacaa ttaccatacc cattaccata cccacaacca   60
caattaccat acccacaacc acaaccattc                                    90
```

```
<210> SEQ ID NO 8
<211> LENGTH: 33
<212> TYPE: PRT
<213> ORGANISM: artificial sequence
<220> FEATURE:
<223> OTHER INFORMATION: Triticum DQ2 epitope

<400> SEQUENCE: 8
```

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 9
<211> LENGTH: 29
<212> TYPE: DNA
<213> ORGANISM: artificial sequence
<220> FEATURE:
<223> OTHER INFORMATION: primer: Gallus gallus Ovalbumin

<400> SEQUENCE: 9
ggctccatcg gtgcagcaag catggaatt                              29

<210> SEQ ID NO 10
<211> LENGTH: 37
<212> TYPE: DNA
<213> ORGANISM: artificial sequence
<220> FEATURE:
<223> OTHER INFORMATION: primer: Gallus gallus Ovalbumin

<400> SEQUENCE: 10
actagttaag gggaaacaca tctgccaaag aagagaa                     37

<210> SEQ ID NO 11
<211> LENGTH: 23
<212> TYPE: DNA
<213> ORGANISM: artificial sequence
<220> FEATURE:
<223> OTHER INFORMATION: primer: based on Triticum DQ8

<400> SEQUENCE: 11
caatacccat caggtgaagg ttc                                    23

<210> SEQ ID NO 12
<211> LENGTH: 32
<212> TYPE: DNA
<213> ORGANISM: artificial sequence
<220> FEATURE:
<223> OTHER INFORMATION: primer: based on Triticum DQ8

<400> SEQUENCE: 12
cgactagtta agcttgtggg ttttcttgtg at                          32

<210> SEQ ID NO 13
<211> LENGTH: 39
<212> TYPE: DNA
<213> ORGANISM: artificial sequence
<220> FEATURE:
<223> OTHER INFORMATION: coding sequence e-tag

<400> SEQUENCE: 13
ggtgctccag ttccataccc agatccactt gaaccacgt                   39

<210> SEQ ID NO 14
<211> LENGTH: 51
<212> TYPE: DNA
<213> ORGANISM: artificial sequence
<220> FEATURE:
<223> OTHER INFORMATION: primer: based on Triticum DQ8

<400> SEQUENCE: 14
ggtgctccag ttccataccc agatccactt gaaccacgtc aatacccatc a     51

<210> SEQ ID NO 15
<211> LENGTH: 32
<212> TYPE: DNA
<213> ORGANISM: artificial sequence
<220> FEATURE:
<223> OTHER INFORMATION: primer: based on Triticum DQ8

```
<400> SEQUENCE: 15
cgactagtta agcttgtggg ttttcttgtg at                                         32

<210> SEQ ID NO 16
<211> LENGTH: 31
<212> TYPE: PRT
<213> ORGANISM: artificial sequence
<220> FEATURE:
<223> OTHER INFORMATION: Triticum DQ8-epitope/e-tag

<400> SEQUENCE: 16

Gly Ala Pro Val Pro Tyr Pro Asp Pro Leu Glu Pro Arg Gln Tyr Pro
1               5                   10                  15

Ser Gly Glu Gly Ser Phe Gln Pro Ser Gln Glu Asn Pro Gln Ala
            20                  25                  30

<210> SEQ ID NO 17
<211> LENGTH: 29
<212> TYPE: DNA
<213> ORGANISM: artificial sequence
<220> FEATURE:
<223> OTHER INFORMATION: primer: Gallus gallus Ovalbumin

<400> SEQUENCE: 17
ggctccatcg gtgcagcaag catggaatt                                             29

<210> SEQ ID NO 18
<211> LENGTH: 37
<212> TYPE: DNA
<213> ORGANISM: artificial sequence
<220> FEATURE:
<223> OTHER INFORMATION: primer: Gallus gallus Ovalbumin

<400> SEQUENCE: 18
actagttaag gggaaacaca tctgccaaag aagagaa                                    37

<210> SEQ ID NO 19
<211> LENGTH: 20
<212> TYPE: DNA
<213> ORGANISM: artificial sequence
<220> FEATURE:
<223> OTHER INFORMATION: Primer: mus musculus Beta-actin

<400> SEQUENCE: 19
acgacatgga gaagatctgg                                                       20

<210> SEQ ID NO 20
<211> LENGTH: 20
<212> TYPE: DNA
<213> ORGANISM: artificial sequence
<220> FEATURE:
<223> OTHER INFORMATION: Primer: mus musculus Beta-actin

<400> SEQUENCE: 20
tcgtagatgg gcacagtgtg                                                       20

<210> SEQ ID NO 21
<211> LENGTH: 24
<212> TYPE: DNA
<213> ORGANISM: artificial sequence
<220> FEATURE:
<223> OTHER INFORMATION: Primer: mus musculus IL-13

<400> SEQUENCE: 21
tcttgcttgc cttggtggtc tcgc                                                  24
```

```
<210> SEQ ID NO 22
<211> LENGTH: 25
<212> TYPE: DNA
<213> ORGANISM: artificial sequence
<220> FEATURE:
<223> OTHER INFORMATION: Primer: mus musculus IL-13

<400> SEQUENCE: 22
gatggcattg caattggaga tgttg                                          25

<210> SEQ ID NO 23
<211> LENGTH: 24
<212> TYPE: DNA
<213> ORGANISM: artificial sequence
<220> FEATURE:
<223> OTHER INFORMATION: Primer: mus musculus eotaxin

<400> SEQUENCE: 23
gggcagtaac ttccatctgt ctcc                                           24

<210> SEQ ID NO 24
<211> LENGTH: 20
<212> TYPE: DNA
<213> ORGANISM: artificial sequence
<220> FEATURE:
<223> OTHER INFORMATION: Primer: mus musculus eotaxin

<400> SEQUENCE: 24
cacttcttct tggggtcagc                                                20

<210> SEQ ID NO 25
<211> LENGTH: 20
<212> TYPE: DNA
<213> ORGANISM: artificial sequence
<220> FEATURE:
<223> OTHER INFORMATION: Primer: mus musculus IL-10

<400> SEQUENCE: 25
tacctggtag gagtgatgcc                                                20

<210> SEQ ID NO 26
<211> LENGTH: 20
<212> TYPE: DNA
<213> ORGANISM: artificial sequence
<220> FEATURE:
<223> OTHER INFORMATION: Primer: mus musculus IL-10

<400> SEQUENCE: 26
gcatagaagc atacatgatg                                                20

<210> SEQ ID NO 27
<211> LENGTH: 20
<212> TYPE: DNA
<213> ORGANISM: artificial sequence
<220> FEATURE:
<223> OTHER INFORMATION: Primer: mus musculus IFN-gamma

<400> SEQUENCE: 27
catagatgtg gaagaaaaga                                                20

<210> SEQ ID NO 28
<211> LENGTH: 20
<212> TYPE: DNA
<213> ORGANISM: artificial sequence
<220> FEATURE:
<223> OTHER INFORMATION: Primer: mus musculus IFN-gamma
```

-continued

```
<400> SEQUENCE: 28
ttgctgaaga aggtagtaat                                                    20

<210> SEQ ID NO 29
<211> LENGTH: 20
<212> TYPE: DNA
<213> ORGANISM: artificial sequence
<220> FEATURE:
<223> OTHER INFORMATION: Primer: mus musculus TGF-Beta

<400> SEQUENCE: 29
ctttaggaag gacctgggtt                                                    20

<210> SEQ ID NO 30
<211> LENGTH: 20
<212> TYPE: DNA
<213> ORGANISM: artificial sequence
<220> FEATURE:
<223> OTHER INFORMATION: Primer: mus musculus TGF-Beta

<400> SEQUENCE: 30
caggagcgca caatcatgtt                                                    20

<210> SEQ ID NO 31
<211> LENGTH: 13
<212> TYPE: PRT
<213> ORGANISM: artificial sequence
<220> FEATURE:
<223> OTHER INFORMATION: DQ8 epitope/e-tag

<400> SEQUENCE: 31

Gly Ala Pro Val Pro Tyr Pro Asp Pro Leu Glu Pro Arg
1               5                   10
```